United States Patent [19]

Olson

[11] Patent Number: 5,015,653

[45] Date of Patent: May 14, 1991

[54] [(5-OXO)-2-PYRROLIDINYL)METHYL]CYCLOHEXANEACETAMIDES, COMPOSITIONS AND USE

[75] Inventor: Gary L. Olson, Westfield, N.J.

[73] Assignee: Hoffmann-La Roche Inc., Nutley, N.J.

[21] Appl. No.: 534,399

[22] Filed: Jun. 7, 1990

Related U.S. Application Data

[63] Continuation-in-part of Ser. No. 377,643, Jul. 10, 1989, abandoned, which is a continuation-in-part of Ser. No. 297,726, Jan. 17, 1989, abandoned.

[51] Int. Cl.$^5$ .................. A61K 31/40; A61K 31/415; C07D 207/12; C07D 403/08
[52] U.S. Cl. ................................. 514/397; 514/424; 548/336; 548/543
[58] Field of Search ............... 548/336, 543; 514/392, 514/397, 424

Primary Examiner—Robert W. Ramsuer
Assistant Examiner—Fiona T. Powers
Attorney, Agent, or Firm—George M. Gould; George W. Johnston; William G. Isgro

[57] ABSTRACT

[(5-oxo-2-pyrrolidinyl)methyl]cyclohexaneacetamides of the formula

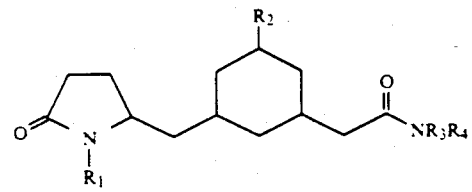

wherein $R_1$ is hydrogen, lower alkyl or aryl-lower alkyl; $R_2$ is hydrogen, lower alkyl, aryl, aryl-lower alkyl,

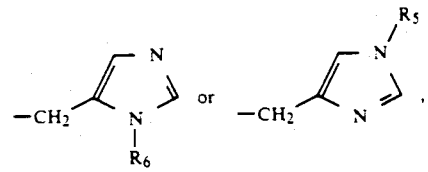

wherein $R_5$ and $R_6$ are hydrogen, lower alkyl or aryl-lower alkyl; $R_3$ and $R_4$, independently, are hydrogen, lower alkyl, or aryl-lower alkyl; and enantiomers, diastereomers, and racemates thereof, and, when $R_2$ is

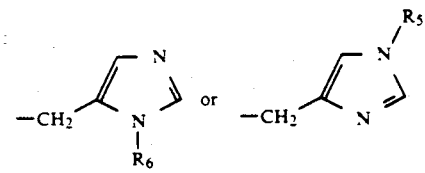

pharmaceutically acceptable acid addition salts thereof, are described.

The compounds of formula I exhibit cognitive enhancement and antiamnestic activity and are therefore useful, for example, in treating memory deficits associated with Alzheimer's disease or age-associated memory impairment.

43 Claims, No Drawings

[(5-OXO)-2-PYRROLIDINYL)METHYL]CYCLOHEXANEACETAMIDES, COMPOSITIONS AND USE

CROSS REFERENCE TO RELATED APPLICATIONS

This application is a continuation-in-part of U.S. patent application Ser. No. 07/377,643, filed July 10, 1989, now abandoned which in turn is a continuation-in-part of U.S. patent application Ser. No. 07/297,726 filed Jan. 17, 1989, now abandoned.

BRIEF SUMMARY OF THE INVENTION

The invention relates to [(5-oxo-2-pyrrolidinyl)methyl]cyclohexaneacetamides of the formula

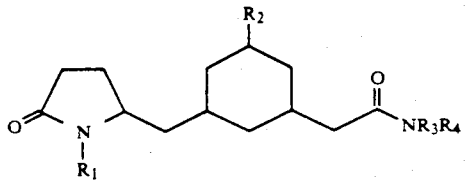

wherein $R_1$ is hydrogen, lower alkyl or aryl-lower alkyl; $R_2$ is hydrogen, lower alkyl, aryl, aryl-lower alkyl,

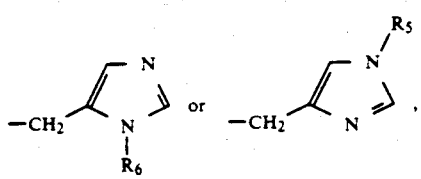

wherein $R_5$ and $R_6$ are hydrogen, lower alkyl or aryl-lower alkyl; $R_3$ and $R_4$, independently, are hydrogen, lower alkyl or aryl-lower alkyl; and enantiomers, diastereomers, and racemates thereof, and, when $R_2$ is

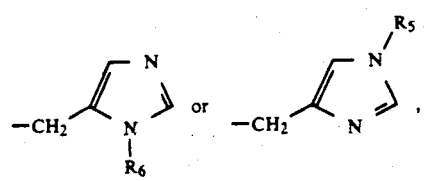

pharmaceutically acceptable acid addition salts thereof.

The compounds of formula I exhibit cognitive enhancement and antiamnestic activity and are therefore useful, for example, in treating memory deficits associated with Alzheimer's disease or age-associated memory impairment.

DETAILED DESCRIPTION OF THE INVENTION

The invention relates to [(5-oxo-2-pyrrolidinyl)methyl]cyclohexaneacetamides of the formula

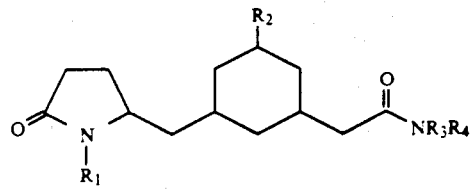

wherein $R_1$ is hydrogen, lower alkyl or aryl-lower alkyl; $R_2$ is hydrogen, lower alkyl, aryl, aryl-lower alkyl,

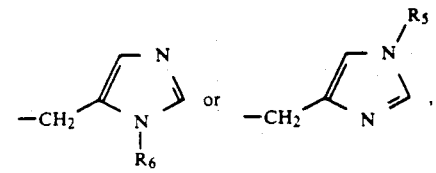

wherein $R_5$ and $R_6$ are hydrogen, lower alkyl or aryl-lower alkyl; $R_3$ and $R_4$, independently, are hydrogen, lower alkyl or aryl-lower alkyl; and enantiomers, diastereomers, and racemates thereof, and, when $R_2$ is

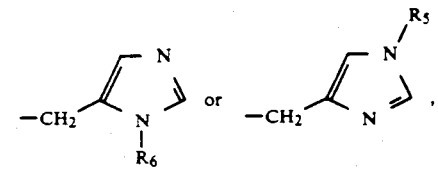

pharmaceutically acceptable acid addition salts thereof.

As used herein, the term "lower alkyl" preferably denotes a straight or branched chain saturated hydrocarbon containing 1 to 7 carbon atoms, for example, methyl, ethyl, propyl, isopropyl, butyl, t-butyl, neopentyl, pentyl, heptyl and the like. The term "lower alkoxy" preferably denotes an alkyl ether group in which the lower alkyl group is as described above, for example, methoxy, ethoxy, propoxy, pentyloxy, isobutoxy, heptoxy and the like. The term "aryl-lower alkyl" preferably denotes a lower alkyl substituted by phenyl or phenyl bearing one or two substituents independently selected from the group consisting of halogen, trifluoromethyl and lower alkyl. Exemplary of aryl-lower alkyl are benzyl, 2-phenylethyl, 2-chlorobenzyl and the like. The term "halogen" denotes bromine, chlorine, fluorine or iodine. The term "aryl" denotes a cyclic aromatic hydrocarbon radical, for example, phenyl or naphthyl, or phenyl or naphthyl bearing one or two substituents independently selected from the group consisting of halogen, trifluoromethyl, lower alkyl, and lower alkoxy.

A preferred group of compounds of the invention comprise those compounds of formula I wherein $R_1$ is hydrogen, lower alkyl or aryl-lower alkyl; $R_2$ is hydrogen, lower alkyl or

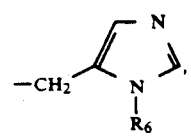

wherein R₆ is hydrogen or aryl-lower alkyl; R₃ and R₄, independently, are hydrogen or lower alkyl and enantiomers and, when R₂ is

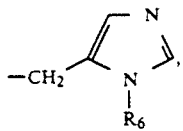

pharmaceutically acceptable acid addition salts thereof.

A more preferred group of compounds of the invention comprise those compounds of formula I wherein R₁ is hydrogen or aryl-lower alkyl; R₂ is lower alkyl or

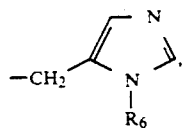

wherein R₆ is hydrogen or aryl-lower alkyl; R₃ and R₄ are hydrogen and, when R₂ is

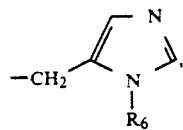

pharmaceutically acceptable acid addition salts thereof.

A still more preferred group of compounds of the invention comprise compounds of the formula

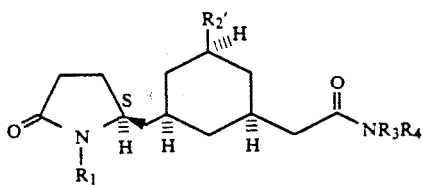
I-A wherein R₂' is hydrogen, alkyl, or aryl-lower alkyl; and R₁, R₃, and R₄ are as previously described, and their enantiomers and racemates.

Particularly preferred are those compounds of formula I-A wherein R₁ is hydrogen or aryl-lower alkyl; R₂' is hydrogen or lower alkyl; R₃ and R₄, independently, are hydrogen and enantiomers thereof.

Also preferred are compounds of the formula

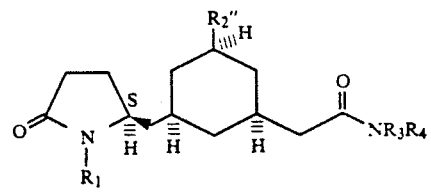
I-B wherein R₂" is

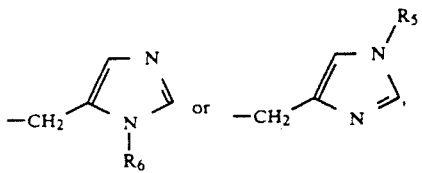

R₁, R₃, R₄, R₅ and R₆ are as previously described, and their enantiomers and racemates and pharmaceutically acceptable acid addition salts thereof. Particularly preferred are compounds of formula I-B wherein R₁ is hydrogen or aryl-lower alkyl; R₂" is

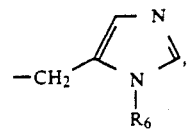

wherein R₆ is hydrogen or aryl lower-alkyl and R₃ and R₄ are hydrogen, and enantiomers, and pharmaceutically acceptable acid addition salts thereof.

Most preferred compounds of formula I of the invention are:

[1R,3R,5S,5(2S)]-3-methyl-5-[[5-oxo-1-(phenylmethyl)-2-pyrrolidinyl]methyl]cyclohexaneacetamide;

[1R,3R,5S,5(2S)]-3-methyl-5-[[5-oxo-2-pyrrolidinyl]methyl]cyclohexaneacetamide;

[1R,3R,5S,5(2S)]-3-methyl-5-[[5-oxo-1-[(4-methoxyphenyl)methyl]-2-pyrrolidinyl]methyl]cyclohexaneacetamide;

[1R,3R,5S,5(2S)]-3-methyl-5-[[5-oxo-1-[(4-chlorophenyl)methyl]-2-pyrrolidinyl]methyl]cyclohexaneacetamide;

[1S,3R,5(2S),5S]-3-[[1-(phenylmethyl)-1H-imidazol-5-yl]methyl]-5-[[5-oxo-1-(phenylmethyl)-2-pyrrolidinyl]methyl]cyclohexaneacetamide;

[1S,3S,5(2S),5S]-3-[[1-(phenylmethyl)-1H-imidazol-5-yl]methyl]-5-[[5-oxo-1-(phenylmethyl)-2-pyrrolidinyl]methyl]cyclohexaneacetamide;

[1S,3RS,5(2S),5S]-3-[[1-(phenylmethyl)-1H-imidazol-5-yl]methyl]-5-[[5-oxo-1-(phenylmethyl)-2-pyrrolidinyl]methyl]cyclohexaneacetamide;

[1S,3R,5(2S),5S]-3-[(1H-imidazol-5-yl)methyl]-5-[[5-oxo-1-(phenylmethyl)-2-pyrrolidinyl]methyl]cyclohexaneacetamide;

[1S,3S,5(2S),5S]-3-[(1H-imidazol-5-yl)methyl]-5-[[5-oxo-1-(phenylmethyl)-2-pyrrolidinyl]methyl]cyclohexaneacetamide;

[1S,3RS,5(2S),5S]-3-[(1H-imidazol-5-yl)methyl]-5-[[5-oxo-1-(phenylmethyl)-2-pyrrolidinyl]methyl]cyclohexaneacetamide;

[1S,3R,5(2S),5S]-3-(1H-imidazol-5-yl-methyl)-5-[(5-oxo-2-pyrrolidinyl)methyl]cyclohexaneacetamide;

[1S,3S,5(2S),5S]-3-(1H-imidazol-5-yl-methyl)-5-[(5-oxo-2-pyrrolidinyl)methyl]cyclohexaneacetamide;

[1S,3RS,5(2S),5S]-3-(1H-imidazol-5-yl-methyl)-5-[(5-oxo-2-pyrrolidinyl)methyl]cyclohexaneacetamide;

[1R3S,3(2S)]-3-[[5-Oxo-1-(phenylmethyl)-2-pyrrolidinyl]methyl]cyclohexaneacetamide;

[1S,3R,5(2S),5S]-3-[(1H-imidazol-5-yl)methyl]-5-[[5-oxo-1-(phenylmethyl)-2-pyrrolidinyl]methyl]cyclohexane-N-methylacetamide;

[1S,3S,5(2S),5S]-3-[(1H-imidazol-5-yl)methyl]-5-[[5-oxo-1-(phenylmethyl)-2-pyrrolidinyl]methyl]cyclohexane-N-methylacetamide;

[1S,3RS,5(2S),5S]-3-[(1H-imidazol-5-yl)methyl]-5-[[5-oxo-1-(phenylmethyl)-2-pyrrolidinyl]methyl]cyclohexane-N-methylacetamide; and

[1S,3R,5(2S),5S]-3-[[1-(phenylmethyl)-1H-imidazol-5-yl)methyl]-5-[[5-oxo-1-(phenylmethyl)-2-pyrrolidinyl]methyl]cyclohexane-N-methylacetamide;

Preferred compounds of the formula I are the following:

[1R,3R,5S,5(2S)]-3-methyl-5-[[5-oxo-1-[(3-methylphenyl)methyl]-2-pyrrolidinyl]methyl]cyclohexaneacetamide;

[1R,3S,5S,5(2S)]-3-methyl-5-[[5-oxo-1-[(3-methylphenyl)methyl]-2-pyrrolidinyl]methyl]cyclohexaneacetamide;

[1R,3RS,5S,5(2S)]-3-methyl-5-[[5-oxo-1-[(3-methylphenyl)methyl]-2-pyrrolidinyl]methyl]cyclohexaneacetamide;

[1R,3R,5S,5(2S)]-3-methyl-5-[[5-oxo-1-methyl-2-pyrrolidinyl]methyl]cyclohexaneacetamide;

[1R,3R,5S,5(2S)]-3-phenylmethyl-5-[[5-oxo-1-(phenylmethyl)-2-pyrrolidinyl]methyl]cyclohexaneacetamide;

[1R,3R,5S,5(2S)]-3-methyl-5-[[5-oxo-1-[2-(phenylethyl)]-2-pyrrolidinyl]methyl]cyclohexaneacetamide;

[1R,3R,5S,5(2R)]-3-methyl-5-[[5-oxo-1-(phenylmethyl)-2-pyrrolidinyl]methyl]cyclohexaneacetamide;

[1S,3S,5R,5(2S)]-3-methyl-5-[[5-oxo-1-(phenylmethyl)-2-pyrrolidinyl]methyl]cyclohexaneacetamide;

[1S,3R,5S,5(2S)]-3-methyl-5-[[5-oxo-1-(phenylmethyl)-2-pyrrolidinyl]methyl]cyclohexaneacetamide;

[1R,3S,5S,5(2S)]-3-methyl-5-[[5-oxo-1-(phenylmethyl)-2-pyrrolidinyl]methyl]cyclohexaneacetamide;

[1S,3S,5S,5(2S)]-3-methyl-5-[[5-oxo-1-(phenylmethyl)-2-pyrrolidinyl]methyl]cyclohexaneacetamide;

Rac.-3-methyl-5-[[5-oxo-1-(phenylmethyl)-2-pyrrolidinyl]methyl]cyclohexaneacetamide;

[1R,3S,3(2R)]-3-[[5-oxo-2-pyrrolidinyl]methyl]cyclohexaneacetamide;

[1S,3R,3(2S)]-3-[[5-oxo-2-pyrrolidinyl]methyl]cyclohexaneacetamide;

[1R,3R,3(2R)]-3-[[5-oxo-2-pyrrolidinyl]methyl]cyclohexaneacetamide; and

[1R,3R,3(2S)]-3-[[5-oxo-2-pyrrolidinyl]methyl]cyclohexaneacetamide;

Other exemplary compounds of the formula I are the following:

[1R,3S,3(2S)]-3-[[5-oxo-1-methyl-2-pyrrolidinyl]methyl]cyclohexaneacetamide;

[1R,3S,3(2S)]-3-[[5-oxo-1-[2-(phenylethyl)-2-pyrrolidinyl]]methyl]cyclohexaneacetamide;

[1R,3S,3(2S)]-3-[[5-oxo-1-(phenylmethyl)-2-pyrrolidinyl]methyl]cyclohexane-N-methylacetamide;

[1R,3S,3(2S)]-3-[[5-oxo-2-pyrrolidinyl]methyl]cyclohexaneacetamide;

[1S,3R,5(2R),5S]-3-[(1H-imidazol-5-yl)methyl]-5-[[5-oxo-1-(phenylmethyl)-2-pyrrolidinyl]methyl]cyclohexaneacetamide;

[1R,3S,5(2S),5R]-3-[(1H-imidazol-5-yl)methyl]-5-[[5-oxo-1-(phenylmethyl)-2-pyrrolidinyl]methyl]cyclohexaneacetamide;

Rac-3-[(1H-imidazol-5-yl)methyl]-5-[[5-oxo-1-(phenylmethyl)-2-pyrrolidinyl]methyl]cyclohexaneacetamide;

[1R,3S,5(2S),5S]-3-[(1H-imidazol-5-yl)methyl]-5-[[5-oxo-1-(phenylmethyl)-2-pyrrolidinyl]methyl]cyclohexaneacetamide;

[1S,3S,5(2S),5S]-3-[(1H-imidazol-5-yl)methyl]-5-[[5-oxo-1-(phenylmethyl)-2-pyrrolidinyl]methyl]cyclohexaneacetamide;

[1R,3S,5(2S),5S]-3-[(1H-imidazol-5-yl)methyl]-5-[[5-oxo-1-(phenylmethyl)-2-pyrrolidinyl]methyl]cyclohexaneacetamide;

[1S,3R,5(2R),5S]-3-[[1-(phenylmethyl)-1H-imidazol-5-yl)methyl]-5-[[5-oxo-1-(phenylmethyl)-2-pyrrolidinyl]methyl]cyclohexaneacetamide;

[1R,3S,5(2S),5R]-3-[[1-(phenylmethyl)-1H-imidazol-5-yl)methyl]-5-[[5-oxo-1-(phenylmethyl)-2-pyrrolidinyl]methyl]cyclohexaneacetamide;

Rac-3-[[1-(phenylmethyl)-1H-imidazol-5-yl)methyl]-5-[[5-oxo-1-(phenylmethyl)-2-pyrrolidinyl]methyl]-cyclohexaneacetamide;

[1R,3S,5(2S),5S]-3-[[1-(phenylmethyl)-1H-imidazol-5-yl)methyl]-5-[[5-oxo-1-(phenylmethyl)-2-pyrrolidinyl]methyl]cyclohexaneacetamide;

[1S,3S,5(2S),5S]-3-[[1-(phenylmethyl)-1H-imidazol-5-yl)methyl]-5-[[5-oxo-1-(phenylmethyl)-2-pyrrolidinyl]methyl]cyclohexaneacetamide;

[1R,3S,5(2S),5S]-3-[[1-(phenylmethyl)-1H-imidazol-5-yl)methyl]-5-[[5-oxo-1-(phenylmethyl)-2-pyrrolidinyl]methyl]cyclohexaneacetamide;

[1S,3R,5(2S),5S]-3-[(1-methyl-1H-imidazol-4-yl)methyl]-5-[[5-oxo-1-(phenylmethyl)-2-pyrrolidinyl]methyl]cyclohexaneacetamide;

[1S,3R,5(2S),5S]-3-[(1-methyl-1H-imidazol-5-yl)methyl]-5-[[5-oxo-1-(phenylmethyl)-2-pyrrolidinyl]methyl]cyclohexaneacetamide;

[1S,3R,5(2S),5S]-3-[(1-methyl-1H-imidazol-4-yl)methyl]-5-[[5-oxo-2-pyrrolidinyl]methyl]cyclohexaneacetamide; and

[1S,3R,5(2S),5S]-3-[(1-methyl-1H-imidazol-5-yl)methyl]-5-[[5-oxo-2-pyrrolidinyl]methyl]cyclohexaneacetamide;

[1R,3R,5S,5(2S)]-3-phenyl-5-[[5-oxo-1-(phenylmethyl)-2-pyrrolidinyl]methyl]cyclohexaneacetamide;

[1S,3R,5(2S),5S]-3-[(1H-imidazol-5-yl)methyl]-5-[[5-oxo-1-[(1-naphthyl)methyl]-2-pyrrolidinyl]methyl]cyclohexaneacetamide The compounds of formula I of the invention may exist as the R and S enantiomers at each of the asymmetric centers, mixtures thereof, or as single diastereomers or single enantiomers. Single diastereomers and single enantiomers are preferred.

The compounds of formula I of the invention, as well as various intermediates which also form part of the invention, are prepared utilizing the process steps hereinafter illustrated and described.

More particularly, the compounds of formula I can be prepared as set forth in Schemes I to XV and as further described.

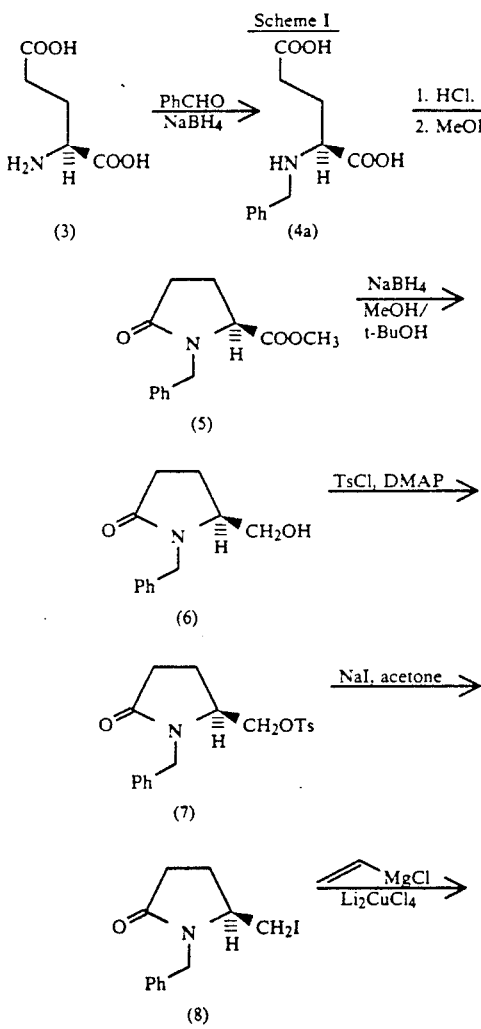

The process set forth in Scheme I comprises the preparation of the intermediate, (S)-5-oxo-1-(phenylmethyl)-2-pyrrolidineacetaldehyde (10a). Thus, L-glutamic acid (3) can be reductively alkylated with benzaldehyde and sodium borohydride to yield the N-(1-phenylmethyl)-L-glutamic acid (4a). Acidification of the solution with hydrochloric acid to pH 3, followed by heating at reflux and then esterification of the crude product with methanol and sulfuric acid in toluene gives the (S)-5-oxo-1-(phenylmethyl)-2-pyrrolidinecarboxylic acid methyl ester (5). Reduction of (5) with sodium borohydride in methanol and t-butanol gives the hydroxymethyl compound characterized by formula (6). The optical purity of (S)-5-(hydroxymethyl)-1-(phenylmethyl)-2-pyrrolidinone (6), can be established by formation of the ester derived from (S)-(−)-α-methoxy-α-(trifluoromethyl)phenylacetic acid ((−)-MTPA) following the procedure of Mosher, et al. [*J. Org. Chem.* 1969, 34, 2543]. Conversion of (6) to the tosylate (7) was accomplished by treatment with p-toluenesulfonyl chloride and 4-dimethylaminopyridine. Treatment of the tosylate (7) with sodium iodide in acetone at reflux gives the iodide (8). Coupling of (8) with vinylmagnesium chloride, catalyzed by dilithium tetrachlorocuprate, leads to the propenyl compound (9), which can be ozonized in methanol with a methyl sulfide workup to yield the aldehyde, (S)-5-oxo-1-(phenylmethyl)-2-pyrrolidineacetaldehyde (10a). All of the steps described in Scheme I can be carried out using DL-glutamic acid or D-glutamic acid as the starting material, if it is desired to prepare enantiomeric or racemic (10a).

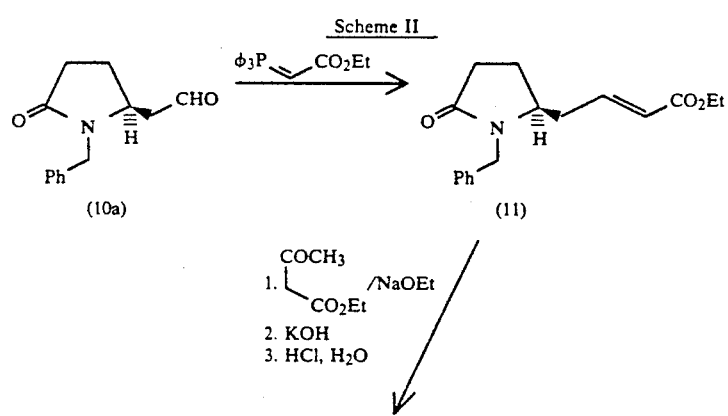

Scheme II

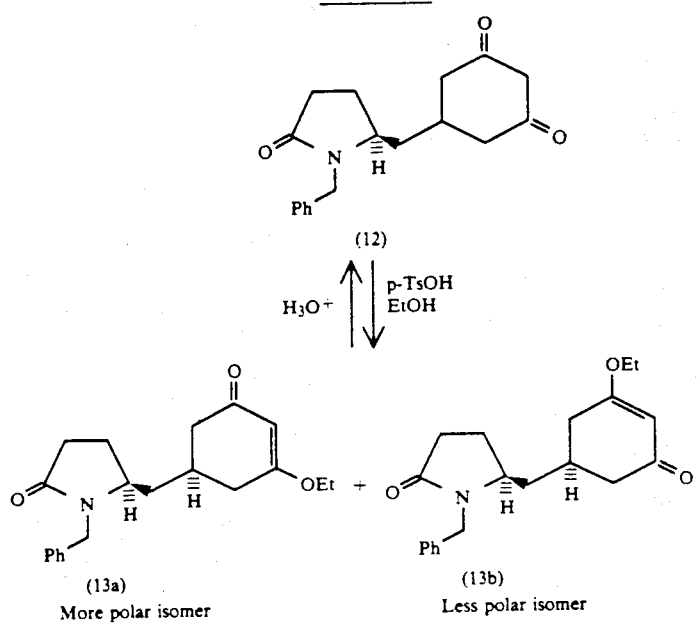

The process set forth in Scheme II comprises the preparation of the intermediates (5S,1R)-5-[(3-ethoxy-5-oxo-3-cyclohexen-1-yl)methyl]-1-(phenylmethyl)-2-pyrrolidinone (13a) and (5S,1S)-5-[(3-ethoxy-5-oxo-3-cyclohexen-1-yl)methyl]-1-(phenylmethyl)-2-pyrrolidinone (13b), starting from (S)-5-oxo-1-(phenylmethyl)-2-pyrrolidineacetaldehyde (10a). Thus, the aldehyde, (S)-5-oxo-1-(phenylmethyl)-2-pyrrolidineacetaldehyde (10a), is treated with ethyl triphenylphosphoranylideneacetate in toluene at 90° C. to give the unsaturated ester (11). Treatment of (11) with ethyl acetoacetate and with sodium ethoxide, followed by hydrolysis and decarboxylation yields the diketone (12). This compound exists as a single enantiomer when derived from a single enantiomer of the aldehyde (10a). Treatment of diketone (12) with ethanol and p-toluenesulfonic acid generates an equal mixture of two diastereomeric ketoenol ethers (13a) and (13b) which are separable by chromatography. The more polar isomer (13a) was shown to have the 5S, 1R stereochemistry, and the less polar isomer (13b) was shown to have the 5S, 1S stereochemistry. This assignment was made by comparison with an X-ray crystal structure of the less polar diastereomer (5S*,1S*) prepared as a racemate by the same processes outlined in Schemes I and II, starting with racemic materials. For the processes described in Schemes III and IV (et seq), only one of the diastereomers (13a or 13b) is used to prepare compounds of the formula I-A or compounds of the formula I-B, respectively. If desired, however, either of the isomers (13a) or (13b) may be recycled to the diketone (12) for the purpose of preparing unequal quantities of either (13a) or (13b). The diketone of formula 12 may be reacted in a similar manner with other alkyl or aralkyl hydroxy compounds to give ketoenol ethers of the formula 13a-1 and 13b-1.

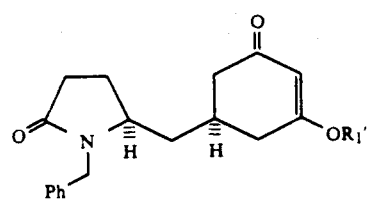

13a-1

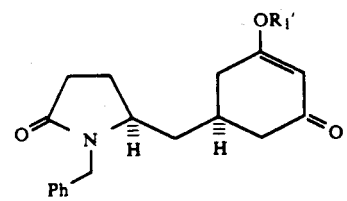

13b-1

Scheme III

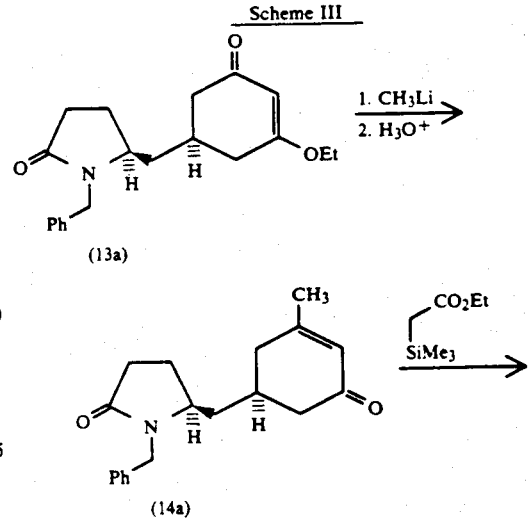

11

-continued
Scheme III

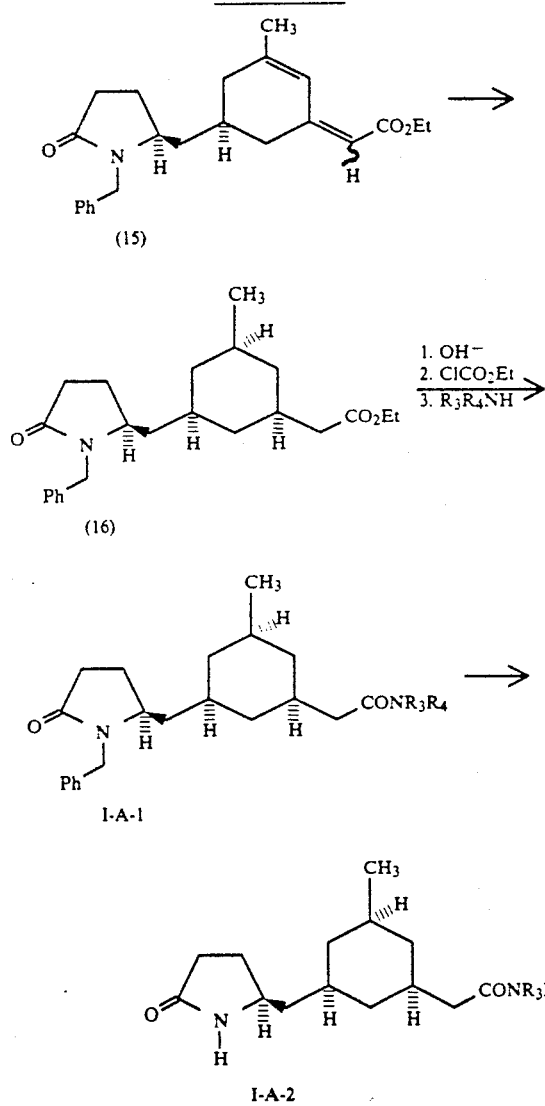

wherein $R_3$ and $R_4$ are as previously described.

The process set forth in Scheme III comprises the preparation of compounds of the formula I-A-1 and I-A-2, starting from (5S,1R)-5-[(3-ethoxy-5-oxo-3-cyclohexen-1-yl)methyl]-1-(phentylmethyl)-2-pyrrolidinone (13a). Thus, the ketoenol ether (13a) is reacted with methyllithium, followed by acid hydrolysis to yield the enone (14a). Treatment of (14a) with ethyl trimethylsilylacetate and lithium diisopropylamide gives the dienoic ester (15). Hydrogenation of (15), for example, over palladium on carbon, gives the saturated ester (16), predominantly as [[1R,3R,5S,5(2S)]-3-methyl-5-[[5-oxo-1-(phenylmethyl)-2-pyrrolidinyl]methyl]-cyclohexaneacetic acid ethyl ester. Smaller quantities (about 15% total) of the other diastereomers are detected by nmr in the crude product. Saponification of the ethyl ester (16) and formation of the active ester with ethyl chloroformate is followed by treatment with ammonia, a primary or secondary amine of the formula $R_3R_4NH$ to give the corresponding 5-(1-phenylmethyl)-substituted cyclohexaneacetamide compounds of the formula I-A-1. Debenzylation of I-A-1, for example, by reduction with sodium in liquid ammonia, yields the corresponding substituted cyclohexaneacetamide compound I-A-2.

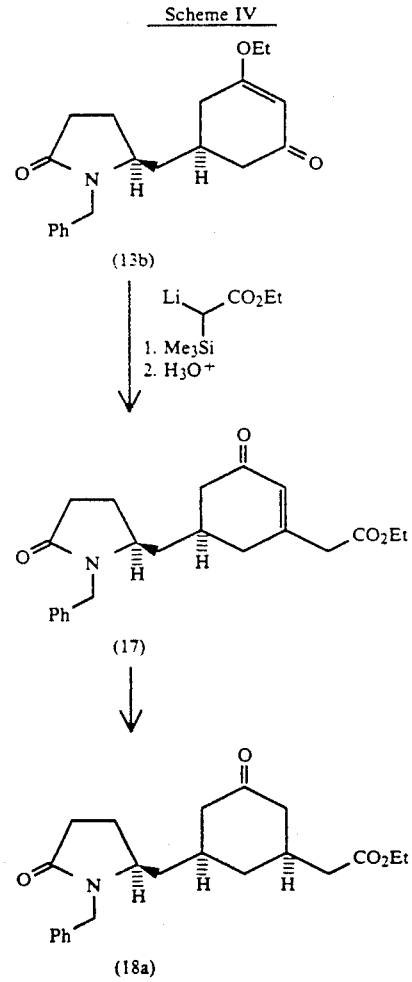

The process set forth in Scheme IV comprises the preparation of the intermediate [1S,5S,5(2S)]-3-oxo-5-[[5-oxo-1-(phenylmethyl)-2-pyrrolidinyl]methyl]cyclohexaneacetic acid ethyl ester (18a), starting from [5S,(1S)]-3-oxo-5-[[5-oxo-1-(phenylmethyl)-2-pyrrolidinyl]methyl]-1-cyclohexene-1-acetic acid ester (13b). Thus, the ketoenolether of formula (13b) is treated with lithio ethyl trimethylsilylacetate (prepared from ethyl trimethylsilylacetate and lithium diisopropylamide), and then hydrolyzed with aqueous acid to yield the enone ester (17). Hydrogenation of (17), for example, over palladium on carbon, produces the saturated ketoester (18a), with the acetic ester side chain predominantly cis to the oxopyrrolidinylmethyl chain. When the compound of formula (13b) is derived from L-glutamic acid, the compound of formula (18a) has the S,S,S-configuration.

Scheme V
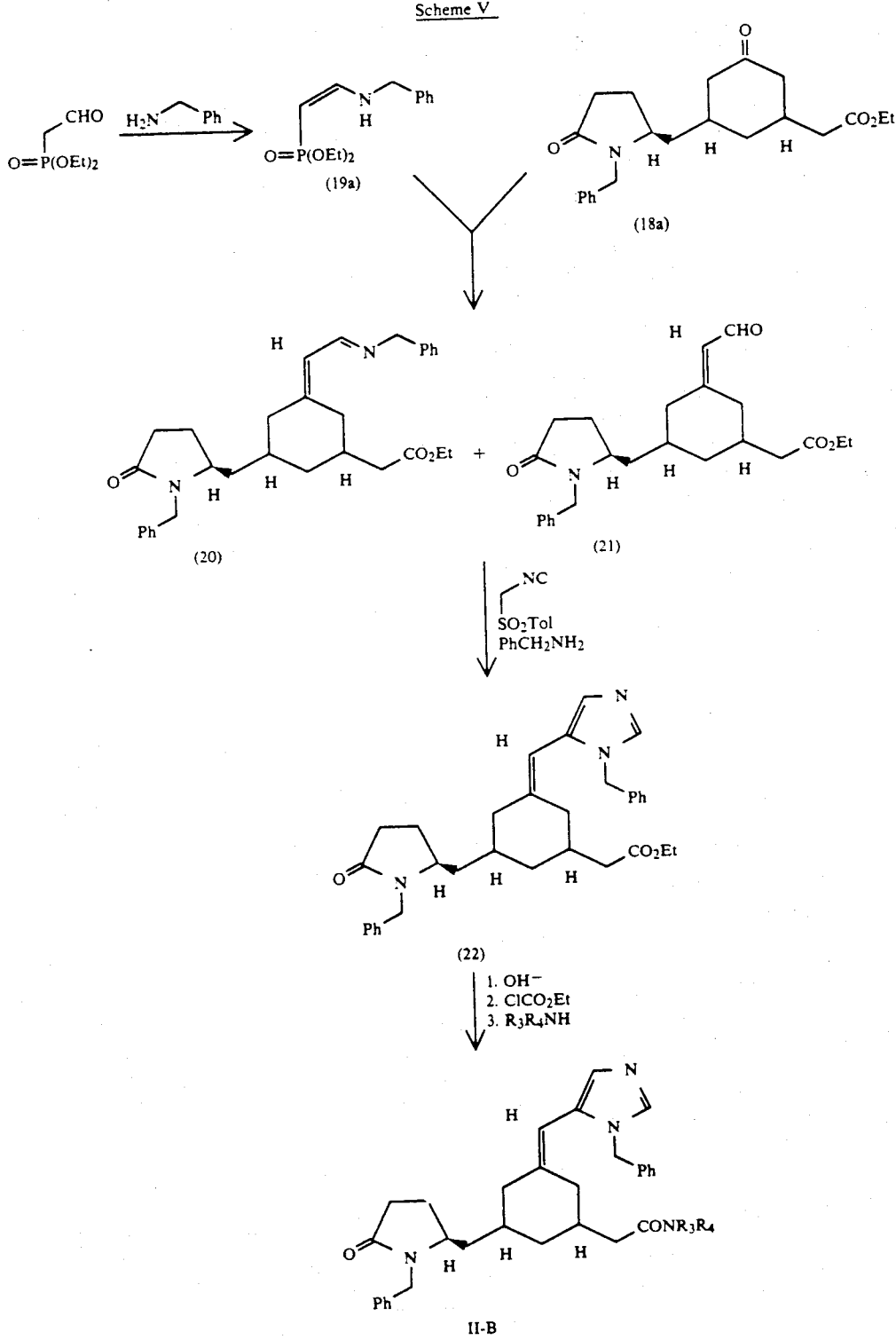
wherein $R_3$ and $R_4$ are as previously described.
It is noted that key intermediates in the preparation of compounds of the formula I, wherein $R_2$ is
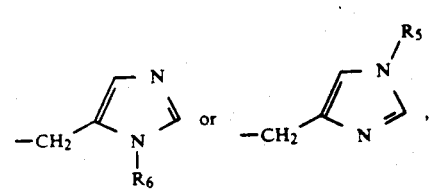

and $R_5$ and $R_6$ are as previously described, are the compounds of the formula

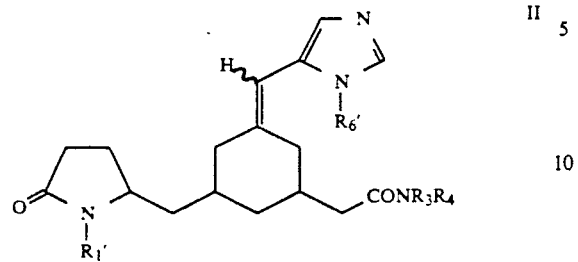

II wherein $R_1'$ is lower alkyl or aryl-lower alkyl and $R_6'$ is lower alkyl or aryl-lower alkyl, and $R_3$ and $R_4$ are as previously described. Compounds of formula II may exist as single enantiomers, racemates, or mixtures of diastereomers, as well as E and Z isomers, or mixtures thereof, and can be prepared in analogy to the process of Scheme V. More particularly, intermediates of the formula II-B are described as being useful for the preparation of the compounds of the formula I-B.

The process set forth in Scheme V comprises the preparation of intermediates of the formula

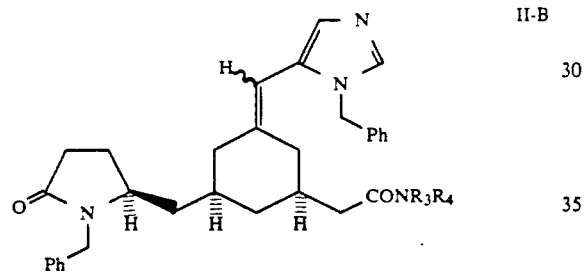

II-B wherein $R_3$ and $R_4$ are as previously described, starting from [1S,5S,5(2S)]-3-oxo-5-[[5-oxo-1-(phenylmethyl)-2-pyrrolidnyl]]methyl]cyclohexaneacetic acid ethyl ester (18a) and [2-[(phenylmethyl)amino]ethenyl]phosphonic acid diethyl ester (19a). More particularly, in Reaction Scheme V, a directed aldol condensation [W. Nagata, et al., *Organic Syntheses*, 1973, 53, 44] is used to elaborate the side chain starting from ketoester (18a). Thus, diethylphosphonoacetaldehyde is converted to the enaminophosphonate (19a) by reaction with benzylamine. The phosphonate (19a), generally used in excess, is converted to its anion with lithium diisopropylamide and condensed with the ketoester (18a) at −40° C. to 0° C. in tetrahydrofuran to yield the unsaturated imine (20) together with the corresponding unsaturated aldehyde (21), which forms during the isolation and chromatography of the crude product. Following the general procedure of van Leusen, et al. [*J. Org. Chem.*, 1977, 42, 1153–1159], the imine-aldehyde mixture is treated with benzylamine and p-toluenesulfonylmethyl isocyanide in methanol at room temperature to yield the unsaturated imidazole ester (22). Saponification of the ester group with ethanolic potassium hydroxide, and amidation via the mixed carbonate with ammonia, a primary or secondary amine of the formula $R_3R_4NH$ at a temperature in the range of from about 0° C. to room temperature, or with ammonia at about 0° C. in chloroform gives the corresponding unsaturated imidazole amides of formula II-B.

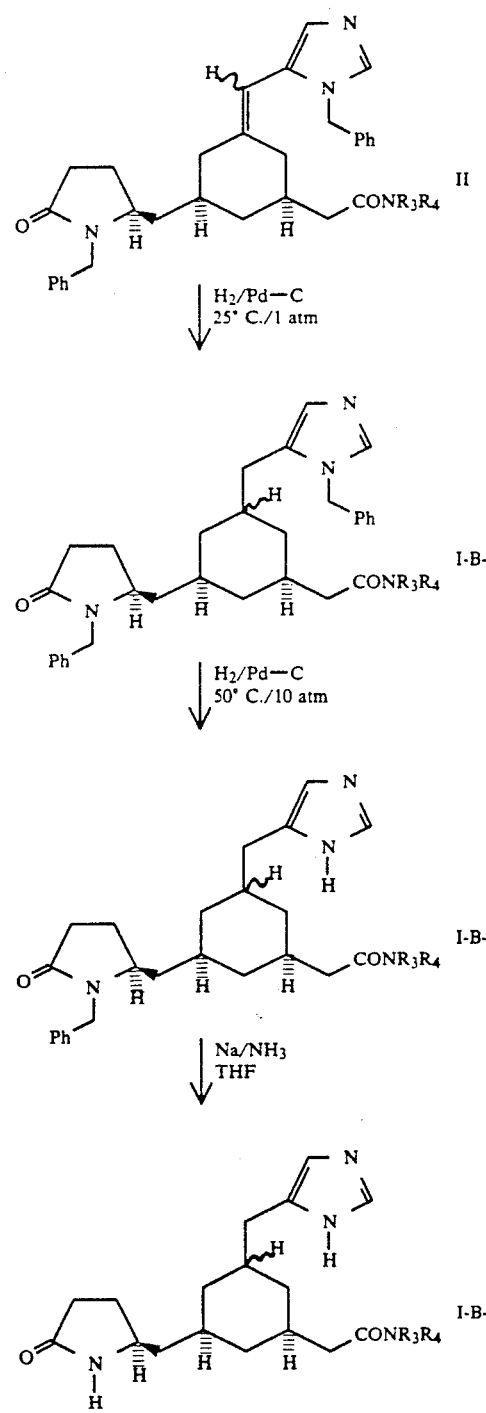

wherein $R_3$ and $R_4$ are as previously described.

The process set forth in Scheme VI comprises the preparation of compounds of the formula I-B-1, I-B-2, and I-B-3, starting from a compound of the formula

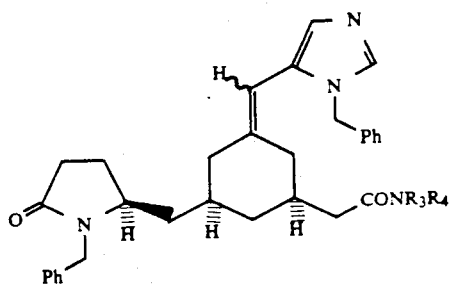

II-B

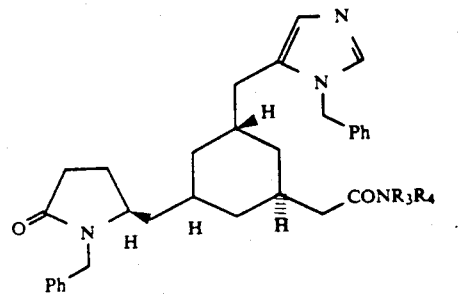

I-B-1b as hereinbefore described. More particularly, in Scheme VI, an unsaturated imidazole amide of formula II-B can be reduced in stages to saturate the double bond and to remove the 1-(phenylmethyl) groups on the imidazole and pyrrolidinone rings selectively. For example, hydrogenation of a compound of formula II-B over 10% palladium on carbon in ethanol at room temperature and at 1 atm pressure yields the corresponding imidazole amides of formula I-B-1. Hydrogenation of a imidazole amide of formula I-B-1, for example, over 10% palladium on carbon in methanol at 50° C. and at 10 atm pressure removes the 1-(phenylmethyl) group from the imidazole ring to yield the corresponding compound of the formula I-B-2. To remove the 1-(phenylmethyl) group from the oxopyrrolidinylmethyl group of a compound of the formula I-B-2, reduction with, for example, sodium metal in refluxing liquid ammonia in tetrahydrofuran is used to prepare the corresponding compound of formula I-B-3. Compounds of formulas I-B-1, I-B-2, and I-B-3 are produced as mixtures of diastereoisomers depending on the catalyst employed for the reduction of the compound of formula II-B. Thus, when the reduction of the compound of formula II-B is performed using 10% palladium on carbon, the diastereoisomers I-B-1a and I-B-1b are produced in approximately equal amounts. When 5% rhodium on carbon is used as the catalyst, the dominant product is the compound of the formula I-B-1b. When Raney nickel is used as the catalyst, the dominant product is the compound of formula I-B-1a. These diastereoisomers can be separated by chromatography, for example, column chromatography on silica gel, to provide the pure diastereomers, I-B-1b and I-B-1a. Each of these pure diastereoisomers may likewise be converted to corresponding pure diastereoisomers of formulas I-B-2a, I-B-2b, I-B-3a, and I-B-3b, as described.

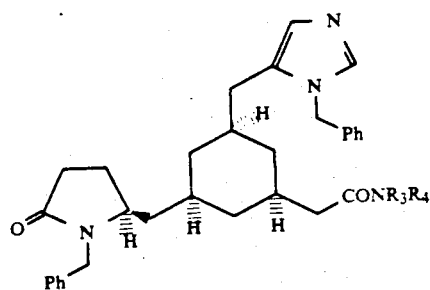

I-B-1a

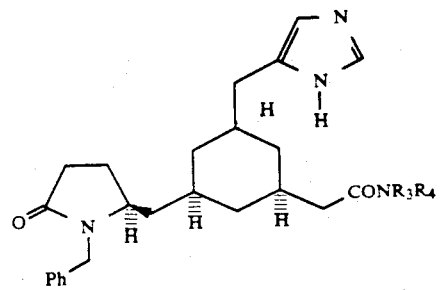

I-B-2a

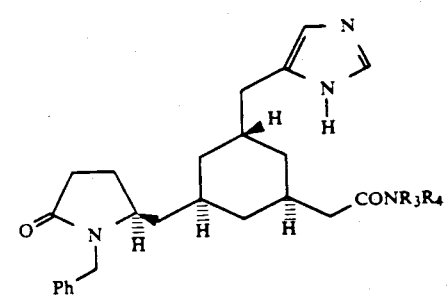

I-B-2b

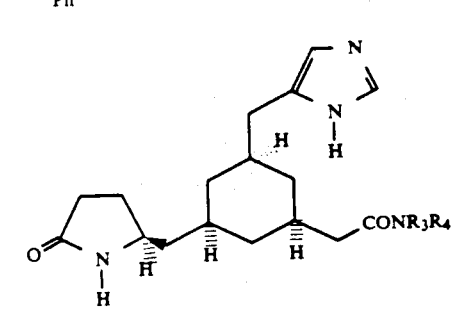

I-B-3a

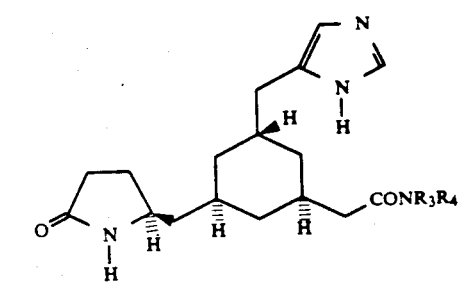

I-B-3b

These products are produced predominantly as single enantiomers when derived from compounds II-B, (18b) and originally from L-glutamic acid. Alternatively, i desired, the use of racemic starting materials, for exam ple, D,L-glutamic acid and mixtures of the diastereom eric ketoenol ethers rac.-13a and rac.-13b, leads to prod ucts of formula I as racemic mixtures of diastereomer

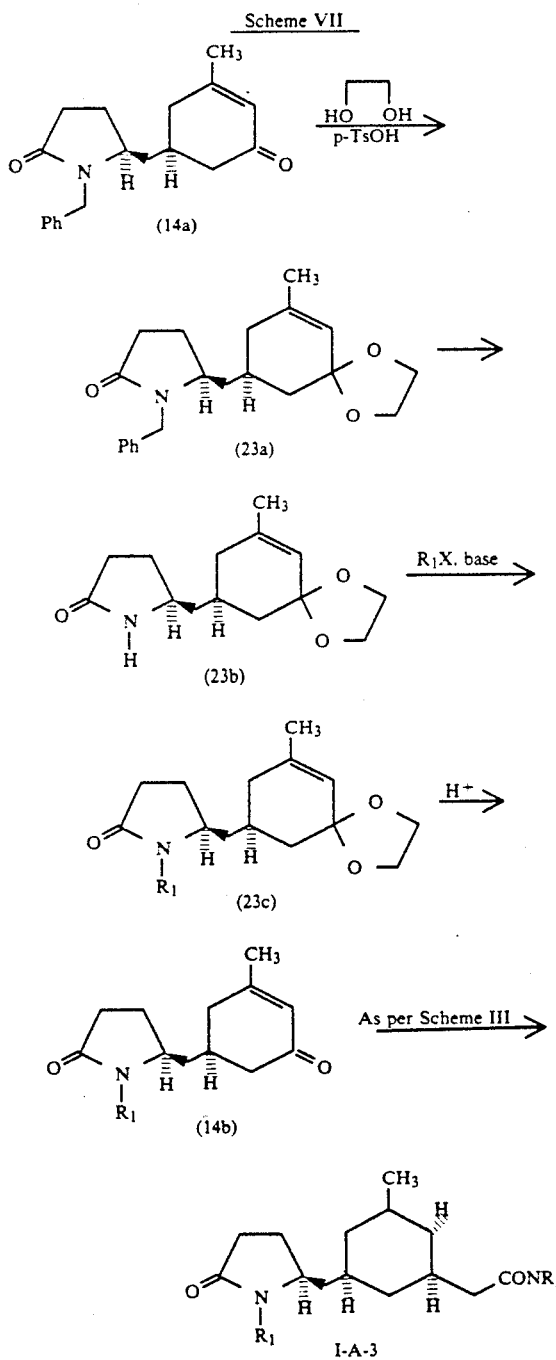

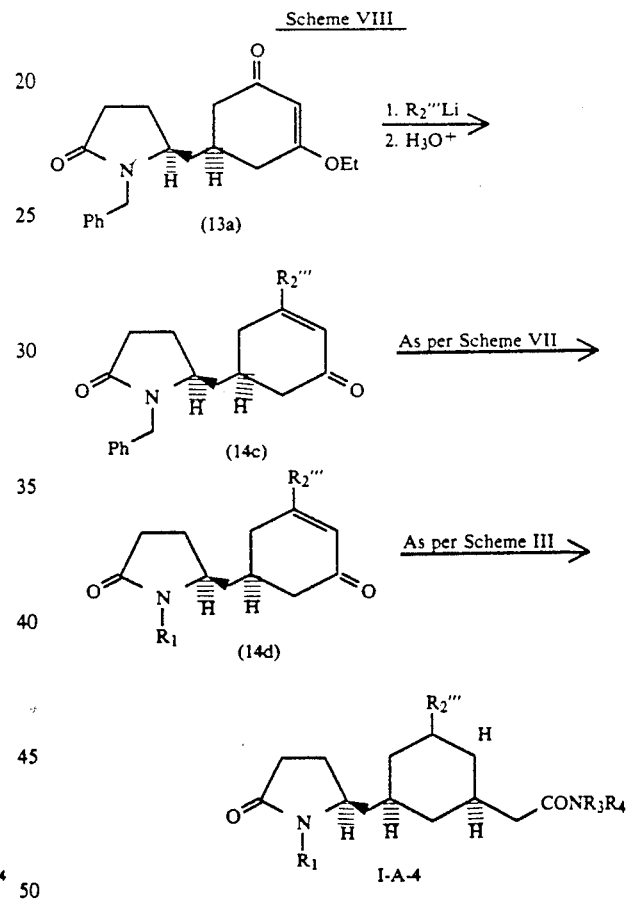

formula (23c). The alkylating agent used in this reaction may be an alkyl halide, for example, methyl iodide, ethyl bromide, butyl bromide and the like; or an aryl-lower alkyl halide, for example, 2-(phenylethyl)bromide, 4-methoxy-1-(phenylmethyl)chloride, 1-(phenylmethyl)bromide and the like. Hydrolysis of the ketal group in (23c) is accomplished by stirring with an acidic ion exchange resin, for example, Amberlyst-15, in aqueous acetone to yield the corresponding substituted enone (14b). The conversion of a compound of the formula (14b) to the corresponding compound of formula I-A-3 is accomplished as previously described in Formula Scheme III.

wherein $R_1$, $R_3$, and $R_4$ are as previously described, and $R_2'''$ is alkyl, aryl, or aryllower alkyl.

The process set forth in Scheme VIII comprises the preparation of compounds of the formula I-A-4, starting from (5S,1R)-5-[(3-ethoxy-5-oxo-3-cyclohexen-1-yl)methyl]-1-(phenylmethyl)-2-pyrrolidinone (13a). More particularly, in Scheme VIII, the ketoenol ether (13a) is treated with an alkyllithium reagent such as methyllithium, phenyllithium, n-butyllithium and the like, or a Grignard reagent, such as methylmagnesium bromide and the like, and then hydrolyzed with aqueous acid to yield an enone of formula (14c). Following the methods outlined in Schemes VII and III starting from 14c in place of 14a, this process leads to compounds of the formula I-A-4.

wherein $R_1$, $R_3$, and $R_4$ are as previously described.

The process set forth in Scheme VII comprises the preparation of compounds of the formula I-A-3, starting from (5S,1R)-5-[(3-methyl-5-oxo-3-cyclohexen-1-yl)methyl]-1-(phenylmethyl)-2-pyrrolidinone. More particularly, in Scheme VII, the enone (14a) is converted to the corresponding ketal (23a) using ethylene glycol and p-toluenesulfonic acid catalyst. Sodium-ammonia reduction of the N-1-(phenylmethyl)ketal (23a) removes the 1-(phenylmethyl) group, giving the lactam ketal (23b). Treatment of (23b) with a base, for example, sodium hydride, and an alkylating agent, for example, $R_1X$, yields the corresponding compound of

Scheme IX

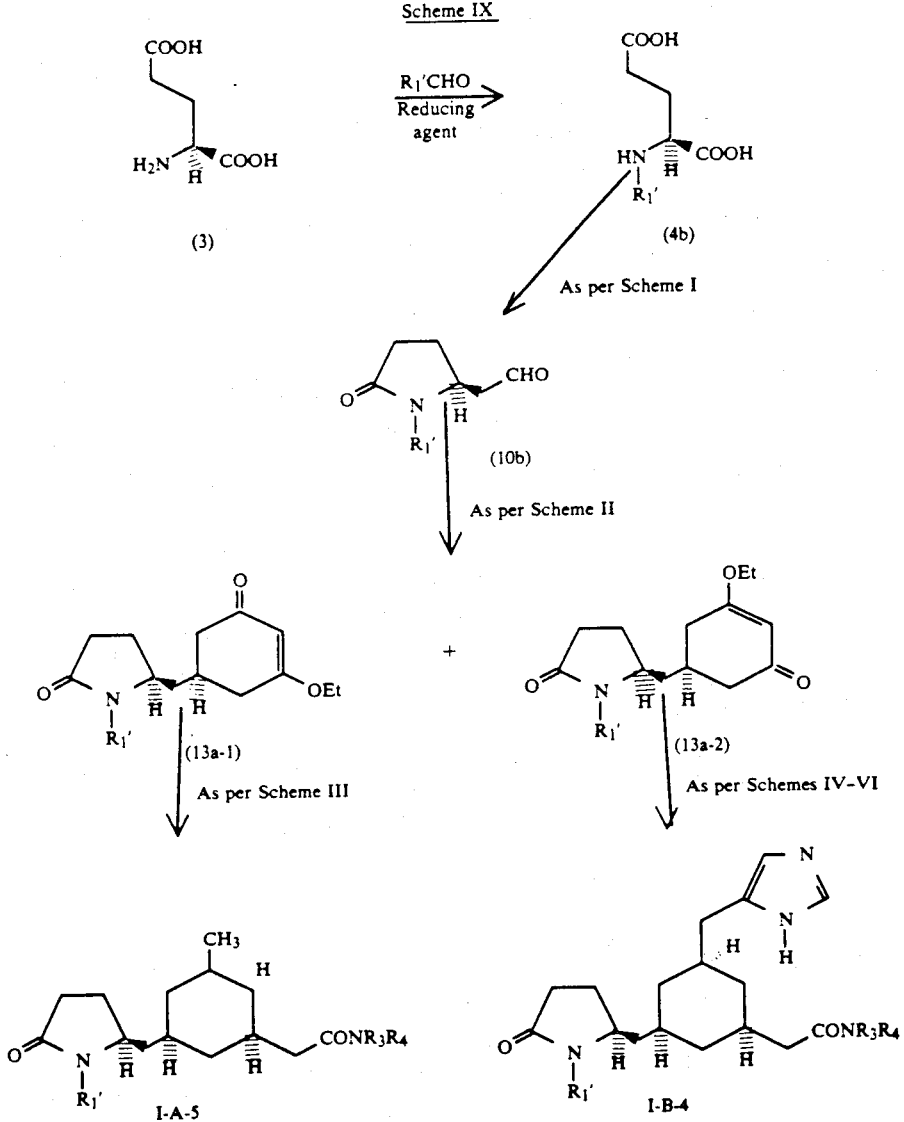

wherein $R_1'$ is alkyl or aryl-lower alkyl, and $R_3$ and $R_4$ are as previously described.

The process set forth in Scheme IX, comprises the preparation of compounds of formula I-A-5 and I-B-4 starting from L-glutamic acid (3). More particularly, in Scheme IX, L-glutamic acid may be reductively alkylated with an aldehyde to yield an N-substituted glutamic acid derivative of the formula (4b). This reductive alkylation may be performed under standard conditions [see, for example, P. Quitt, et al., *Helv. Chim. Acta*, 1963, 46, 327-333]. Remaining conversions are performed as described in Schemes I, II, III, and IV-VI.

Scheme X

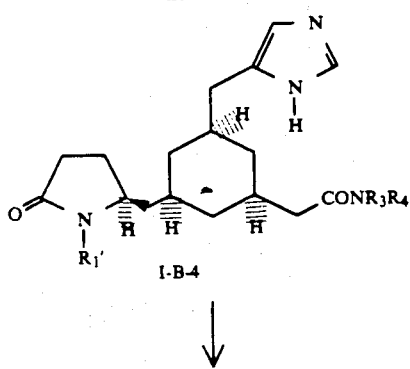

Scheme X

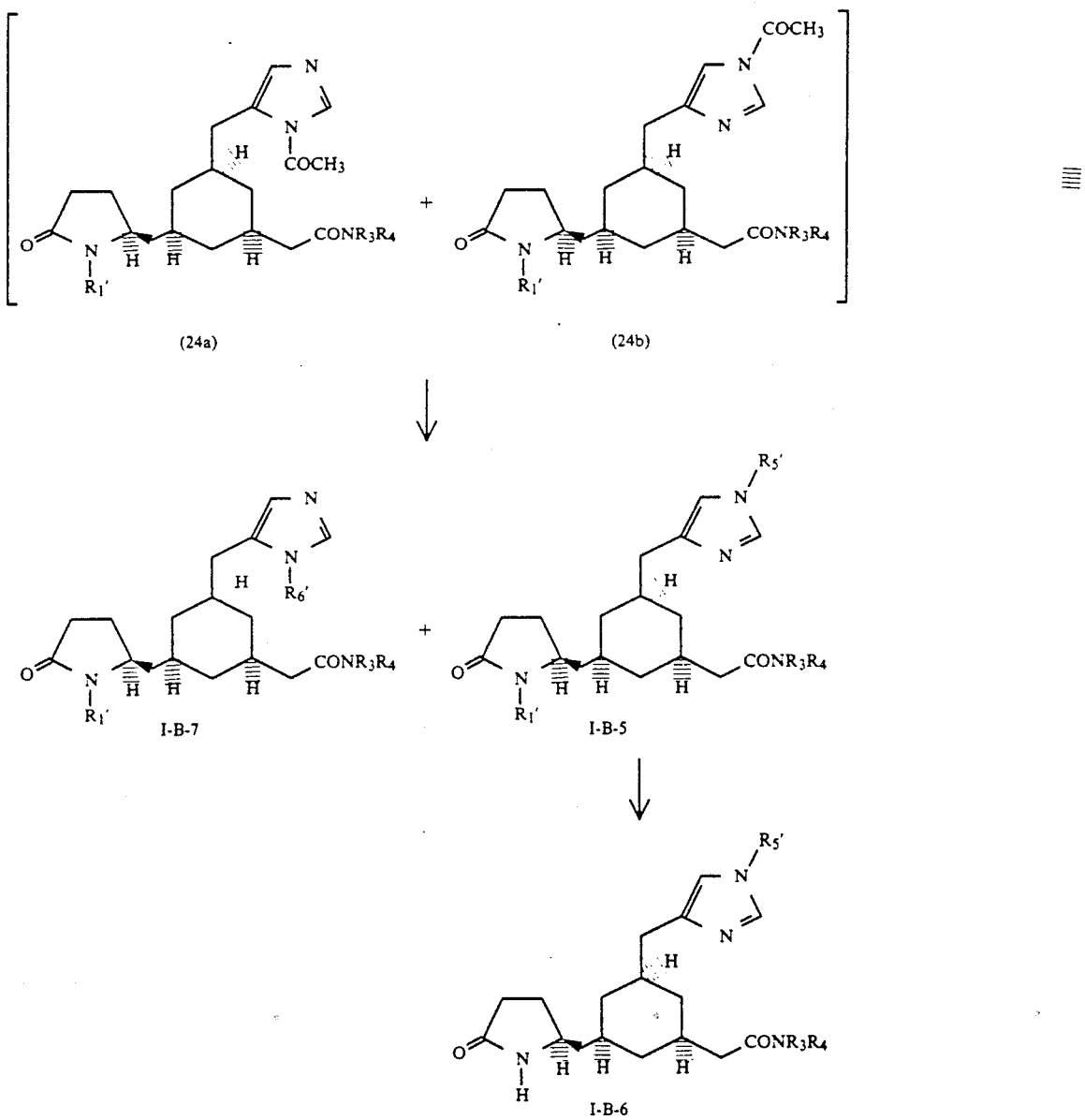

wherein $R_5'$ is alkyl or aryl-lower alkyl and $R_1'$, $R_3$, $R_6'$ and $R_4$ are as previously described.

The process set forth in Scheme X comprises the preparation of compounds of the formula I-B-5 and I-B-7 starting from a compound of the formula I-B-4, and the further conversion of the compound of formula I-B-5 to the compound of formula I-B-6. More particularly, in Scheme X, an imidazole amide of formula I-B-4 is treated with acetyl chloride in the presence of a base, such as 4-dimethylaminopyridine and the like, at a temperature in the range of room temperature to about 50° C. to yield a mixture of the corresponding acetates of formulas 24a and 24b. The mixture is then treated with an alkyl or aryl-lower alkyl halide, for example, with methyl iodide followed by alkaline hydrolysis, to yield the corresponding compound I-B-5 or I-B-7. If desired, the mixture of compounds of formulas I-B-5 and I-B-7 may be separated, for example, by chromatography, to yield the individual compounds, or the acetates 24a and 24b can be separated prior to treatment with the halide to provide the individual compounds of the formula I-B-5 and I-B-7. Conversion of the compound of formula I-B-5 wherein $R_1'$ is benzyl may be accomplished by treatment with sodium in liquid ammonia to yield a compound of the formula I-B-6.

Scheme XI

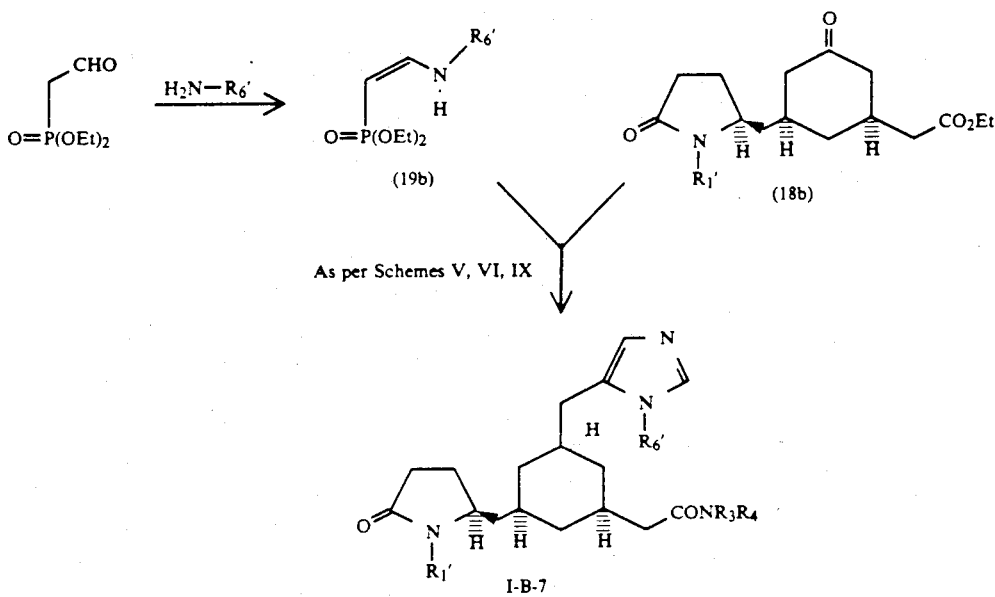

wherein $R_1'$, $R_3$, $R_4$ and $R_6'$ are as previously described.

The process set forth in Scheme XI comprises the preparation of compounds of the formula I-B-7 starting from diethylphosphonoacetaldehyde and a primary amine. More particularly, in Scheme XI, diethylphosphonoacetaldehyde may be condensed with a primary amine of the formula $H_2N$-$R_6'$ to form a phosphonoenamine of the formula (19b). A number of these compounds are found to exist in equilibrium with tautomeric forms in which the imine form, rather than the enamine form, predominates. [See, for example, W. Nagata, et al., *Organic Syntheses*, 1973, 53, 44]. These substituted phosphonoenamine/imine compounds undergo directed aldol condensation with a ketoester of formula (18a) as described in Scheme V, employing an amine of the formula $R_6 \cdot NH_2$ instead of benzylamine as the base used in the addition of tosylmethylisocyanide. The products are converted to the corresponding compounds of formula I-B-7 as outlined in Schemes VI, and IX.

Scheme XII

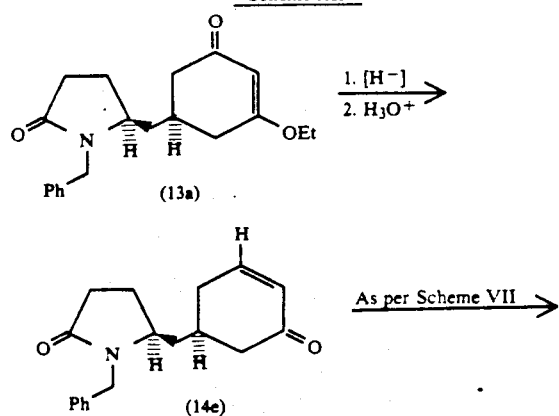

-continued
Scheme XII

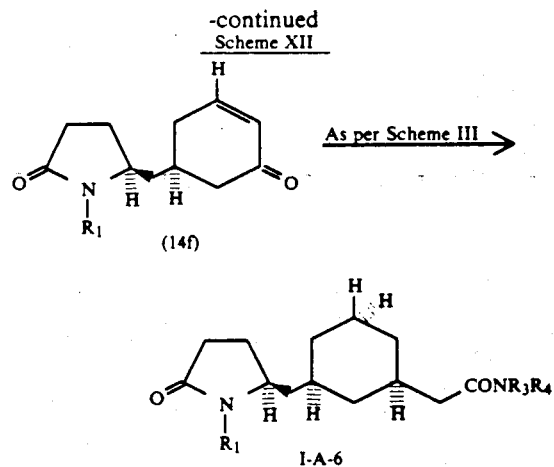

wherein $R_1$, $R_3$, and $R_4$ are as previously described.

The process set forth in Scheme XII comprises the preparation of compounds of the formula I-A-6, starting from (5S,1R)-5-[(3-ethoxy-5-oxo-3-cyclohexen-1-yl)methyl]-1-(phenylmethyl)-2-pyrrolidinone (13a). More particularly, in Scheme XII, hydride reduction of the ketoenol ether 13a with a selective hydride, for example, sodium borohydride-cerium chloride [Luche, J. L.; Rodriguez-Hahn, L.; Crabbe, P. *J. Chem. Soc. Chem. Commun.*, 1978, 601–602] followed by acid hydrolysis gives the enone of formula 14e. The methods for the further transformations of 14e to the corresponding compound of formula I-A-6 are described in Schemes VII and III.

Scheme XIII

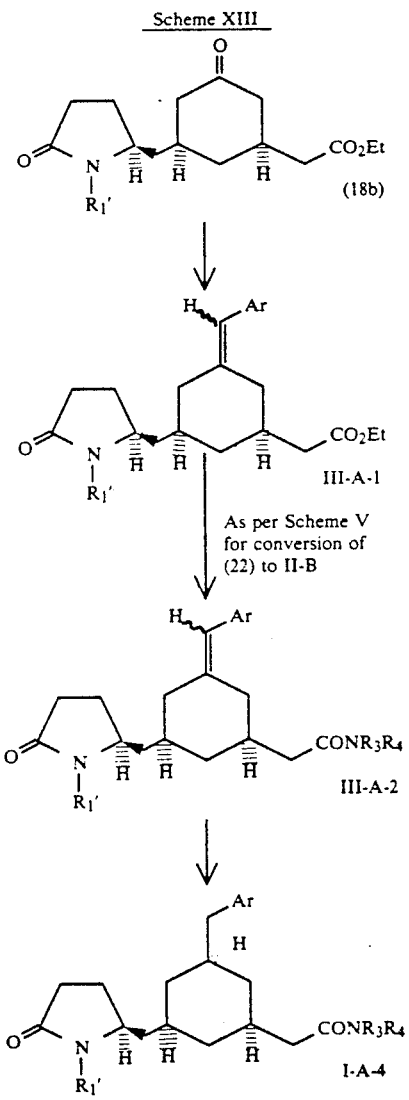

wherein $R_1'$, $R_3$, and $R_4$ are as hereinbefore described; Ar is an aryl group.

The process set forth in Scheme XIII comprises an alternative method for the preparation of compounds of the formula I-A-4. More particularly, in Scheme XIII, a compound of the formula 18b is reacted with a Wittig reagent derived from an aryl-methyl halide, for example, benzyltriphenylphosphorane, or a Peterson reagent, for example benzyltrimethylsilyllithium, in an inert organic solvent, such as toluene or tetrahydrofuran, at a temperature of from about 25° C. to reflux (for the Wittig reagent) or about −70° C. to about room temperature (for the Peterson reagent) to yield the alkylidene compound of the formula III-A-1. This product is formed as a mixture of E- and Z-isomers. The ester compound of formula III-A-1 is converted to the amide compound III-A-2 following the procedures described in Scheme V for the conversion of (22) to II-B, that is, by saponification of the ethyl ester III-A-1 and formation of the active ester with, for example, ethyl chloroformate, followed by treatment with ammonia, a primary or secondary amine of the formula $R_3R_4NH$ to give the corresponding compounds of the formula III-A-2. Reduction of the double bond in the compound of the formula III-A-2, for example, by catalytic hydrogenation over 10% palladium on carbon in ethyl acetate, yields the compound of formula I-A-4.

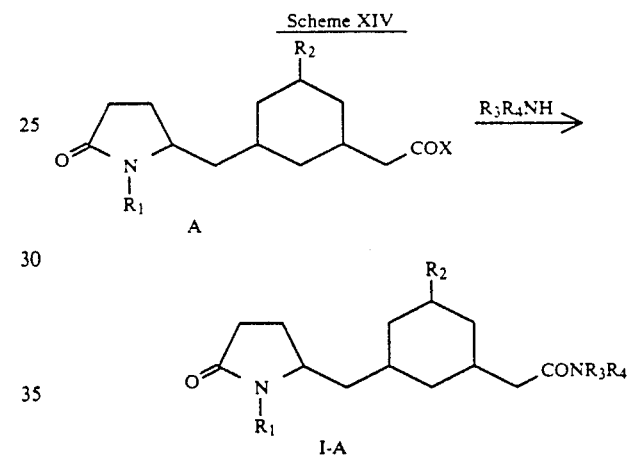

wherein $R_1$, $R_2$, $R_3$, and $R_4$ are as previously described, and COX is a carboxylic acid or activated derivative thereof.

Scheme XIV describes a general procedure for the preparation of a compound of formula I-A. In Scheme XIV, a compound of formula A wherein COX is an acid or activated derivative thereof (for example, an acyl halide, mixed anhydride, or active ester), is treated with an amine of the formula $R_3R_4NH$, wherein $R_3$ and $R_4$ are as previously described, to give a compound of formula I-A. This reaction is further described and exemplified in Scheme III.

Scheme XV

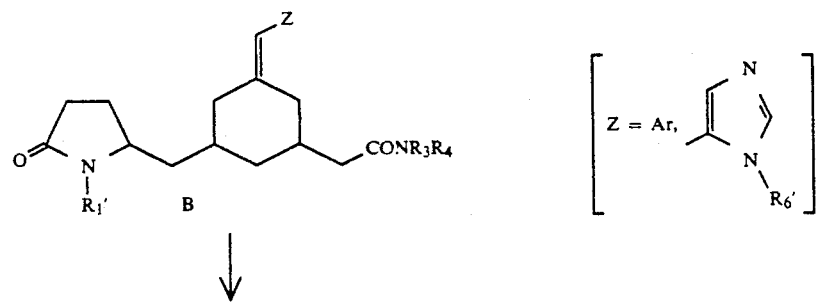

-continued
Scheme XV

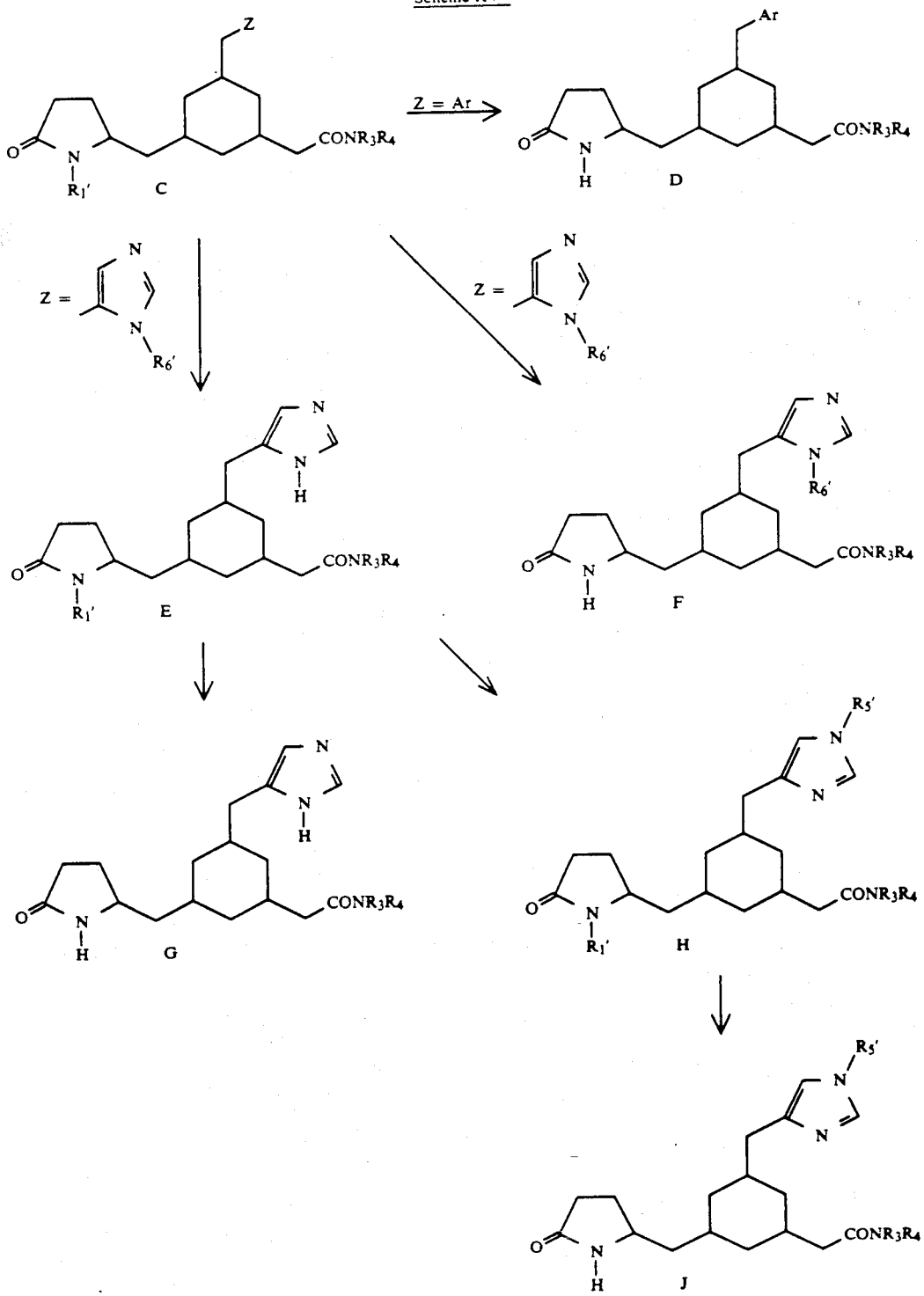

wherein $R_1'$, $R_3$, $R_4$, $R_5'$, and $R_6'$ are as previously described, and Z is aryl or

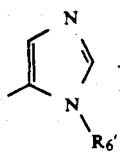

Scheme XV describes a general procedure for the preparation of compounds of formula I, further characterized by the formulas C, D, E, F, G, H, and J. In this procedure, an unsaturated compound of formula B is first reduced by catalytic hydrogenation, for example, at 1 atmosphere of hydrogen over a palladium catalyst at room temperature to afford a saturated compound of the formula C. In the case where Z in the compound of the formula C is an aryl group, the compound of formula D may be prepared by removal of the substituent $R_1'$ when that group is benzyl, for example, by reduction with sodium in liquid ammonia. In the case where Z in the compound of the formula C is

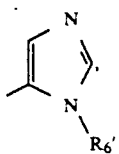

a compound of the formula E may be prepared by removal of the group $R_6'$, for example, when $R_6'$ is benzyl, it may be removed by catalytic hydrogenolysis over palladium catalysts at temperatures and pressures that are higher than those used for the hydrogenation of compounds of the formula B. Alternatively, when $R_6'$ is an alkyl group, and $R_1'$ is a benzyl group, reduction of the compound of formula C with, for example, sodium in liquid ammonia affords the compound of formula F. Compounds of the formula G may be prepared from compounds of the formula E when $R_1'$ is benzyl by reduction, for example, with sodium in liquid ammonia. Additionally, compounds of the formula H may be prepared by alkylation of the imidazole ring of a compound of the formula E. A compound of the formula J may be prepared from a compound of the formula H by removal of the $R_1'$ group, for example, when $R_1'$ is a benzyl group, by reduction of the compound of formula H with, for example, sodium in liquid ammonia. The reactions and processes described in Scheme XV are further described and exemplified in Schemes V, VI, IX, X, XI, and XIII, and constitute an aspect of this invention.

It is understood that preferably, but not necessarily, any intermediate prepared in Schemes I-XV may be isolated utilizing known procedures, for example, precipitation, crystallization, chromatography or the like, prior to use in the next reaction step. The end-products of formula I are isolated by similar known procedures.

Various intermediates utilized in the processes described in Schemes I-XV can be further characterized by the following formulas and also form a part of this invention:

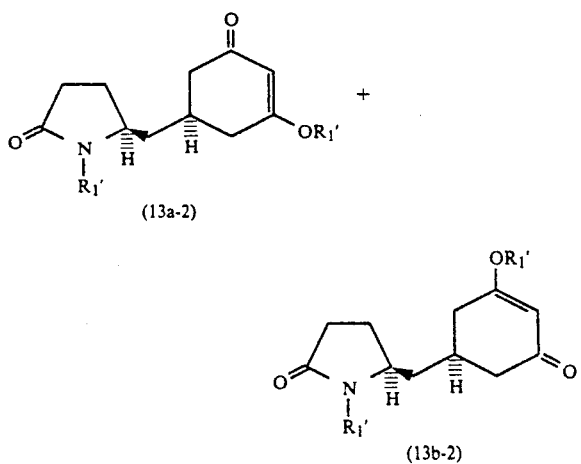

and compounds of the formula:

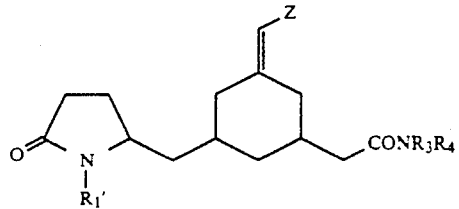

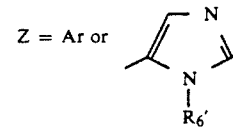

as well as the oxo compound of formula 18b:

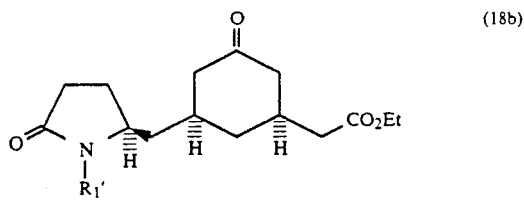

The compounds of formula I, including their enantiomers, diastereomers and racemates, form acid addition salts when $R_2$ is

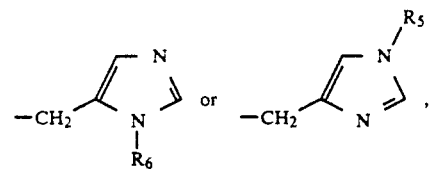

and such salts are also within the scope of this invention. Thus, the above compounds of formula I, including their enantiomers, diastereomers and racemates, form pharmaceutically acceptable addition salts with, for example, both pharmaceutically acceptable organic and inorganic acids, such as acetic acid, succinic acid, formic acid, methanesulfonic acid, p-toluenesulfonic acid, hydrochloric acid, nitric acid, phosphoric acid, sulfuric acid and the like.

The compounds of formula I exhibit central nervous system activity. In particular, the compounds of formula I exhibit cognitive enhancement and antiamnestic activity in warm-blooded mammals. Accordingly, the compounds of formula I are useful in treating psychogeriatric disorders, for example, in treating memory deficits associated with age-associated memory impairment or Alzheimer's disease. The activity of the compounds of formula I which makes them useful in treating psychogeriatric disorders can be demonstrated in warm-blooded animals, in accordance with known procedures, as hereinafter set forth.

METHODS

The test animals were male C57B1/10 mice, weighing 17-21 grams at the time of testing. Mice were housed in groups of 10 and had ad lib access to food and water. Mice of this strain appear to be deficient in learning the water maze task and are therefore suitable for use in drug evaluation. [Symons, J. P., Davis, R. E., and Marriott J. G. Life Sciences, 1988, 42, 375-383.]

The Morris water maze task requires an animal to attend to spatial cues in order to locate the position of a hidden platform submerged underwater. [Morris, B. G. Learning and Motivation, 1981, 12, 239-260, and Symons, J. P., Davis, R. E., and Marriott J. G. Life Sciences, 1988, 42, 375-383.] The maze consisted of a 60 cm × 60 cm × 60 cm transparent plexiglas chamber filled to a depth of 30 cm, leaving 30 cm of wall extended up from the water surface. The water was made opaque by the addition of powdered milk. The water temperature was maintained at 20° C. Both distal cues (i.e., standard room objects) and proximal cues (that is, 20 cm × 22 cm unique black and white patterns pasted to the center of each of the four walls of the maze) were used. The submerged platform, 8 × 8 cm, 1 cm below the water's surface was positioned near one of the four corners of the maze.

Each animal was given four consecutive trials (maximum of 2 min/trial, and a 10 sec intertrial interval) to locate the position of the hidden platform. On each trial the animal was placed into the water at the opposite corner to that of the submerged platform. Between trials animals were removed from the water and placed on a dry surface under a heat lamp before the start of the next trial. The time required for each animal to locate the platform on each of the four trials was recorded (latency). The mean total latency of the four trials was used as the score for a given animal.

DRUG PREPARATION

The test compounds and TRH (thyrotropin releasing hormone, pGlu-His-ProNH$_2$), were dissolved in saline and administered by the intraperitoneal or oral routes 30 minutes prior to testing. Mice received 10 ml/kg of body weight. A group of mice in each of the experiments with test compounds received a 0.1 mg/kg dose of TRH and thus served as a positive control treatment condition.

TABLE I

Activity of Representative Compounds in the Morris Water Maze

| Test Compound | Active Dose Range (mg/kg) or Active Period | Procedure/Route |
| --- | --- | --- |
| TRH | 0.1–0.3 | Dose-Response (IP) |
| Compound A | 0.1 | Dose-Response (IP) |
| Compound B | 0.003–0.1 | Dose-Response (IP) |
| Compound C | 0.3–1.0 | Dose-Response (IP) |
| Compound D | 0.3–1.0 | Dose-Response (IP) |
| Compound E | 0.01–0.3 | Dose-Response (IP) |
| Compound F | 0.3–1.0 | Dose-Response (IP) |
| Compound G | 1.0–10.0 | Dose-Response (IP) |
| Compound H | 0.00003–10.0 | Dose-Response (IP) |
| Compound I | 0.03–3 | Dose-Response (IP) |
| Compound B | 0.03–0.1 | Dose-Response (PO) |
| Compound E | 0.003–0.3 | Dose-Response (PO) |
| Compound H | 0.00003–10.0 | Dose-Response (PO) |
| Compound B | 30–60 min. | Time-Response (PO) |
| Compound E | 30–60 min. | Time-Response (PO) |

Compound A - [1R, 3R, 5S, 5(2S)]-3-Methyl-5-[[5-oxo-2-pyrrolidinyl]methyl]-cyclohexaneacetamide
Compound B - [1R, 3R, 5S, 5(2S)]-3-Methyl-5-[[5-oxo-1-(phenylmethyl)-2-pyrrolidinyl]methyl]-cyclohexaneacetamide
Compound C - [1R, 3RS, 5(2S), 5S]-3-[[1-(Phenylmethyl)-1H-imidazol-5-yl]methyl]-5-[[5-oxo-1-(phenylmethyl)-2-pyrrolidinyl]methyl]cyclohexaneacetamide
Compound D - [1S, 3RS, 5(2S), 5S]-3-(1H-Imidazol-5-yl-methyl)-5-[[5-oxo-2-pyrrolidinyl]methyl]cyclohexaneacetamide
Compound E - [1S, 3RS, 5(2S), 5S]-3-[(1H-Imidazol-5-yl)methyl]-5-[[5-oxo-1-(phenylmethyl)-2-pyrrolidinyl]methyl]cyclohexaneacetamide
Compound F - [1S, 3R, 5(2S), 5S]-3-[[1-(Phenylmethyl)-1H-imidazol-5-yl-]methyl]-5-[[5-oxo-1-(phenylmethyl)-2-pyrrolidinyl]methyl]cyclohexaneacetamide
Compound G - [1S, 3S, 5(2S), 5S]-3-[[1-(Phenylmethyl)-1H-imidazol-5-yl-]methyl]-5-[[5-oxo-1-(phenylmethyl)-2-pyrrolidinyl]methyl]cyclohexaneacetamide
Compound H - [1S, 3R, 5(2S), 5S]-3-[(1H-Imidazol-5-yl)methyl]-5-[[5-oxo-1-(phenylmethyl)-2-pyrrolidinyl]methyl]cyclohexaneacetamide
Compound I - [1S, 3S, 5(2S), 5S]-3-[(1H-Imidazol-5-yl)methyl]-5-[[5-oxo-1-(phenylmethyl)-2-pyrrolidinyl]methyl]cyclohexaneacetamide Since the compounds of formula I have four asymmetric centers (three, if R$_2$ is H), there are theoretically $2^4 = 16$ possible isomers. The procedures described herein are capable of producing single enantiomers, diastereomers, or racemates thereof, depending upon whether the starting material is L-glutamic acid, D-glutamic acid, or DL-glutamic acid. Similarly, the procedures described herein are capable of controlling the relationship between the various asymmetric centers, such that other diastereomers are produced. In addition, minor diastereomers may be produced in steps wherein the major diastereomer is separated and used for subsequent steps. In general, diastereomers differ in their physical properties, and mixtures of diastereomers can be separated, for example, by chromatography or crystallization. Formula I, as described herein, embraces all such isomeric forms.

A composition containing a therapeutically effective amount of a compound of formula I, an enantiomer, a diastereomer or a racemate or a salt thereof can be administered by methods well known in the art. Thus, a compound of formula I, or a salt thereof can be administered either singly or with other therapeutic agents. For oral administration they can be administered in the form of tablets, capsules, for example, in admixture with talc, starch, milk sugar or other inert ingredients, that is, pharmaceutically acceptable carriers, or in the form of aqueous solutions, suspensions, elixirs or aqueous alcoholic solutions, for example, in admixture with sugar or other sweetening agents, flavoring agents, colorants, thickeners and other conventional pharmaceutical excipients. For parenteral administration, they can be administered in solution or suspension, for example, as an aqueous or peanut oil solution or suspension using excipients and carriers conventional for this mode of administration.

In the practice of the invention, the dose of a compound of formula I or a salt thereof to be administered and the frequency of administration will be dependent on the potency and duration of activity of the particular compound of formula I or salt thereof to be administered and on the route of administration, as well as the severity of the condition, age of the mammal to be treated and the like. Oral doses of a compound of formula I or a salt thereof contemplated for use in practicing the invention are in the range of from about 0.05 to about 200 mg per day, preferably from about 0.5 to about 20 mg either as a single dose or in divided doses.

The examples which follow further illustrate the invention. All temperatures are in degrees Centigrade, unless otherwise specified.

EXAMPLE 1

(S)-5-Oxo-1-(phenylmethyl)-2-pyrrolidinecarboxylic acid methyl ester

L-Glutamic acid, monosodium salt (250 g, 1.33 mol) was added at room temperature to a solution of sodium hydroxide (53.6 g, 1.34 mol) in 550 mL of water. To the resulting solution was added benzaldehyde (142.3 g, 1.34 mol). The mixture was stirred and cooled to 10° C. and sodium borohydride (15.2 g, 0.409 mol) was added in portions, keeping the temperature at 10°-15° C. The mixture was stirred for 30 min, and another portion of benzaldehyde (7.5 g, 0.07 mol) was added. After 10 min, a second portion of sodium borohydride (3.7 g, 0.10 mol) was added as before. The mixture was then allowed to stir at room temperature overnight. The solution was washed with methylene chloride (250 mL, discarded), and acidified to pH 3 with 6N HCl. The paste, consisting of N-(phenylmethyl)-L-glutamic acid, was diluted with 500 mL of $H_2O$ and heated to reflux overnight. The resulting solution was cooled to room temperature and extracted with chloroform. The combined extracts were washed with brine, dried over $Na_2SO_4$, and concentrated on a rotary evaporator to give 160 g (55% yield) of (S)-5-oxo-1-(phenylmethyl)-2-pyrrolidinecarboxylic acid as a white solid.

The crude (S)-5-oxo-1-(phenylmethyl)-2-pyrrolidinecarboxylic acid (160 g, 0.73 mol) was dissolved in 300 mL of toluene and 550 mL of methanol. To the solution was added 9 mL of conc $H_2SO_4$ and the solution was heated to reflux overnight. The solution was cooled in an ice bath and neutralized to pH 5 with 25% NaOH, followed by adding 50 mL of saturated sodium bicarbonate to bring the solution to pH 7. The methanol was removed on a rotary evaporator and the residue was diluted with 500 mL of water and extracted with methylene chloride. The combined extracts were washed with brine and dried over $MgSO_4$. Evaporation of the solvent afforded 132 g of (S)-5-oxo-1-(phenylmethyl)-2-pyrrolidinecarboxylic acid methyl ester as an oil which was >95% pure by NMR. $^1$H NMR ($CDCl_3$) δ 2.0–2.6 (m, 4H, $CH_2$'s), 3.68 (s, 3 H, $CH_3$), 3.95 (dd, 1 H, J=4,9 Hz, H-4), 4.02 and 5.03 (AB, 2 H, $J_{gem}$=16 Hz, $CH_2Ph$), 7.2–7.4 (m, 5 H, arom).

EXAMPLE 2

(S)-5-(Hydroxymethyl)-1-(phenylmethyl)-2-pyrrolidinone

A solution of (S)-5-oxo-1-(phenylmethyl)-2-pyrrolidinecarboxylic acid methyl ester (132 g, 0.556 mol) in 600 mL of t-butanol was cooled to ca. 18° C. Sodium borohydride (41 g, 1.12 mol) was added in one portion. To the suspension was added over 45 min 425 mL of methanol. The reaction was kept at 15° C. during the addition, during which time hydrogen gas was evolved. After the addition, the mixture was kept at 20° C. until hydrogen evolution had subsided, and was allowed to stand at room temperature overnight. The solvents were removed on a rotary evaporator, and the residue was dissolved in 1 L of water and acidified to pH 7.5 with 2N HCl. The mixture was extracted with methylene chloride and the combined extracts were washed with 2N HCl and brine, and dried over $Na_2SO_4$. Evaporation of the solvent afforded 96.3 g of crude product, which was recrystallized once from toluene to give 89.5 g (77% yield) of (S)-5-(hydroxymethyl)-1-(phenylmethyl)-2-pyrrolidinone as a white solid, mp 82°–4° C. (toluene). $^1$H NMR ($CDCl_3$) δ 1.92 and 1.94 (dd, J=6.5 Hz, 1 H, OH), 1.96–2.11 (m, 2 H, $CH_2$), 2.36–2.61 (m, 2 H, $COCH_2$), 3.48–3.78. (m, 3 H, $CH_2O$ and CH), 4.29 and 4.81 (AB, $J_{gem}$=15 Hz, 2 H, $CH_2Ph$), 7.26–7.35 (m, 5 H, phenyl). $[α]^{25}_D$= +116° (c 1.07, methanol). Anal. Calcd for $C_{12}H_{15}NO_2$: C, 70.22; H, 7.37; N, 6.75. Found: C, 70.06; H, 7.41; N 6.75.

The optical purity of the (S)-5-(hydroxymethyl)-1-(phenylmethyl)-2-pyrrolidinone was established by formation of the ester derived from (S)-(−)-α-methoxy-α-(trifluoromethyl)phenylacetic acid ((−)-MTPA) following the procedure of Mosher, et al. (J. Org. Chem. 1969, 34, 2543). A single diastereomeric ester, as judged by $^1$H NMR and TLC, was obtained, and could readily be differentiated from the diastereomeric mixture (by the doubling of the $CH_2N$ and $CH_2O$ signals in the $^1$H NMR) produced when racemic 5-(hydroxymethyl)-1-(phenylmethyl)-2-pyrrolidinone was used to form the (−)-MTPA ester.

EXAMPLE 3

(S)-5-[[(4-Methylphenyl)sulfonyl]methyl]-1-(phenylmethyl)-2-pyrrolidinone

To a solution of (S)-5-(hydroxymethyl)-1-(phenylmethyl)-2-pyrrolidinone (143.7 g, 0.70 mol) in 3.5 L of methylene chloride was added 4-dimethylaminopyridine (94.1 g, 0.77 mol), and p-toluenesulfonyl chloride (133.5 g, 0.70 mol). The solution was stirred at room temperature overnight, then washed with cold 1N HCl (600 mL), saturated sodium bicarbonate (500 mL), and brine, and was dried over sodium sulfate ($Na_2SO_4$). Evaporation of the solvent gave (S)-5-[[(4-methylphenyl)sulfonyl]methyl]-1-phenylmethyl)-2-pyrrolidinone (244.6 g, 97.2% yield) as a white solid, mp 79°–80° C. (ether). $^1$H NMR ($CDCl_3$) δ 1.86 (m, 1 H, CH of $CH_2$), 2.08 (m, 1 H, CH of $CH_2$), 2.37 (m, 1 H, CH of $CH_2$), 2.47 (s, 3 H, $CH_3$), 2.49 (m, 1 H, CH of $CH_2$), 3.61 (m, 1 H, NCH), 3.79 and 4.91 (AB, 2 H, $J_{gem}$=15 Hz, $NCH_2$), 3.95 and 4.02 (AB of ABX, 2 H, $J_{vic}$=4 and 4 Hz, $J_{gem}$=10.5 Hz, —$CH_2O$—), 7.13–7.27 (m, 5H, phenyl), 7.37, 7.73 (AA'BB', 4 H, $J_{ortho}$=8 Hz, aromatic). IR ($CHCl_3$) 1680, 1368, 1172, 700 cm$^{-1}$. MS (EI) m/e 359 (M$^+$). Anal. Calcd for $C_{19}H_{21}NO_4S$: C, 63.49; H, 5.89; N, 3.90. Found: C, 63.52; H, 5.95; N, 3.72.

EXAMPLE 4

(S)-5-Iodomethyl-1-(phenylmethyl)-2-pyrrolidinone

A mixture of (S)-5-[[(4-methylphenyl)sulfonyl]methyl]-1-(phenylmethyl)-2-pyrrolidinone (244.5 g, 0.68 mol), sodium iodide (305 g, 2.03 mol), and 3 L of acetone was refluxed and stirred overnight. The suspension was cooled to 10° C. and was filtered. The salts were rinsed with three 250-mL portions of acetone, and the acetone washes and filtrate were concentrated on a rotary evaporator to a thick slurry. Methylene chloride (1.5 L) was added and the white precipitate was filtered off and washed with methylene chloride. The filtrate was dried over magnesium sulfate ($MgSO_4$), filtered through a pad of silica gel, and concentrated on a rotary evaporator to give 196.8 g (92% yield) of (S)-5-iodomethyl-1-(phenylmethyl)-2-pyrrolidinone as an off-white solid, mp 92°–94° C. (cyclohexane). $^1$h NMR (CDCl₃) δ 1.7-2.75 (m, 4 H, CH₂), 3.18-3.28 (m, 2 H, CH₂I), 3.42 (m, 1 H, NCH), 3.98 and 4.05 (AB, 2 H, J$_{gem}$=15 Hz, CH₂Ph), 7.20 (m, 5 H, phenyl). [α]$^{25}_D$= +12.11 (c 0.35, methanol). Anal. Calcd for C₁₂H₁₄NOI: C, 45.73; H, 4.48; N, 4.44. Found: C, 45.58; H, 4.35; N, 4.22.

EXAMPLE 5

(S)-1-(Phenylmethyl)-5-(2-propenyl)-2-pyrrolidinone

To a solution of (S)-5-iodomethyl-1-(phenylmethyl)-2-pyrrolidinone (31.5 g, 0.1 mol) in 250 mL of anhydrous tetrahydrofuran was added a solution of Li₂CuCl₄ (7.5 mL of a 0.1M solution in tetrahydrofuran; prepared from anhydrous lithium chloride (85 mg) and anhydrous cupric chloride (134.5 mg) in 10 mL of tetrahydrofuran). The solution was cooled to −78° C. and vinyl magnesium chloride (200 mL of 1M solution in tetrahydrofuran) was added over a 25 min period. After stirring for 1 h at −78° C., a second portion of vinyl magnesium chloride (200 mL of 1M solution) was added as before. After stirring for another 1 h, a third portion (200 mL of 1M solution) was added as before, and the mixture was stirred at −78° C. overnight. The cold solution was then poured onto 1.5 kg of ice and was acidified with 100 mL of 6N hydrochloric acid (HCl). The mixture was extracted with methylene chloride, washed with saturated sodium bicarbonate and brine, and dried over MgSO₄. The solution was concentrated on a rotary evaporator to give 23.8 g of crude (S)-1-(phenylmethyl)-5-(2-propenyl)-2-pyrrolidinone as a brown oil. The crude product was chromatographed on 700 g of silica gel, eluting with 50% ethyl acetate in hexanes to give 14.2 g (66% yield) of the pure (S)-1-(phenylmethyl)-5-(2-propenyl)-2-pyrrolidinone as a colorless oil. ¹H NMR (CDCl₃) δ 1.7-2.75 (m, 6 H, CH₂'s), 3.51 (m, 1 H, NCH), 4.99 and 5.02 (AB, J$_{gem}$=15 Hz, 2 H, CH₂Ph), 5.0-5.2 (m, 2 H, vinyl H), 5.4-5.9 (m, 1 H, vinyl H), 7.25-7.40 (m, 5 H, phenyl).

EXAMPLE 6

(S)-5-Oxo-1-(phenylmethyl)-2-pyrrolidineacetaldehyde

A solution of (S)-1-(phenylmethyl)-5-(2-propenyl)-2-pyrrolidinone (44.8 g, 0.208 mol) in 800 mL of 1:1 methanol:methylene chloride was cooled to −78° C. and was ozonized using a Welsbach ozonizer for 6.5 h, approximately 1 h longer than the time required to observe a light blue color of ozone in the solution. Excess ozone was flushed out of the system with oxygen, and the solution was treated with methyl sulfide (80 mL). The solution was then allowed to come to room temperature and to stand overnight. The solvents were removed on a rotary evaporator, and the residual liquid was dissolved in 700 mL of methylene chloride, washed with water, and dried over Na₂SO₄. Evaporation of the solvent afforded 43.0 g of crude (S)-5-oxo-1-(phenylmethyl)-2-pyrrolidineacetaldehyde. Chromatography on silica gel (1 kg) eluting with 4% methanol in methylene chloride afforded 38 g (84.4% yield) of the pure (S)-5-oxo-1-(phenylmethyl)-2-pyrrolidineacetaldehyde. ¹H NMR (CDCl₃) δ 1.60-2.60 (m, 4 H, CH₂), 2.77 (half of ABX, 1 H, J$_{gem}$=18, J$_{vic}$=4 Hz, CH₂CHO), 3.98 (m, 1 H, NCH), 4.10 and 4.82 (AB, 2 H, J$_{gem}$=15 Hz, CH₂Ph), 7.15-7.40 (m, 5 H, phenyl), 9.65 (s, 1 H, CHO).

EXAMPLE 7

(E)-4-[2(R)-5-Oxo-1-(phenylmethyl)-2-pyrrolidinyl]-2butenoic acid, ethyl ester

To a solution of (S)-5-oxo-1-(phenylmethyl)-2-pyrrolidineacetaldehyde (38g, 0.175 mol) in 700 mL of toluene was added ethyl triphenylphosphoranylideneacetate (73.0 g, 0.21 mol) and the mixture was heated to 90° C. for 5.5 h. The solvent was removed on a rotary evaporator and the residue was slurried with 50 mL of ethyl acetate. The bulk of the precipitate of triphenylphosphine oxide was removed by filtration, and the filter cake was washed with 150 mL of 1:1 ethyl acetate:hexane. The solution was concentrated on a rotary evaporator, mixed with 200 mL of 3:1 hexane:ethyl acetate, and allowed to stand at room temperature for 72 h. The crystalline triphenylphosphine oxide was filtered off, and the residual oil (63 g) was chromatographed on 2 kg of silica gel, eluting with ethyl acetate to give 48 g (95.6% yield) of (E)-4-[2(R)-5-oxo-1-(phenylmethyl)-2-pyrrolidinyl]-2-butenoic acid, ethyl ester as an oil. ¹H NMR (CDCl₃) δ 1.30 (t, J=5.5 Hz, CH₃), 1.60-2.50 (m, 6H, CH₂'s), 3.60 (m, 1 H, NCH), 3.96 and 4.99 (AB, J$_{gem}$=15 Hz, CH₂Ph), 4.15 (q, J=5.5 Hz, 2 H, OCH₂), 5.85 (d, J=16 Hz, 1 H, C-2 vinyl H), 6.74 and 6.80 (dt, J=8,16 Hz, 1 H, C-3 vinyl H), 7.20-7.40 (m, 5 H, phenyl).

EXAMPLE 8

(S)-5-[[Oxo-1-(phenylmethyl)-2-pyrrolidinyl]methyl]-1,3-cyclohexanedione

Sodium metal (7.82 g, 0.34 g-atom) was dissolved in 1.1 L of ethanol. Ethyl acetoacetate (44.2 g, 0.34 mol) and (E)-4-[2(R)-5-oxo-1-(phenylmethyl)-2-pyrrolidinyl]-2-butenoic acid, ethyl ester (66.0 g, 0.23 mol) were added and the solution was refluxed and stirred overnight. The solvent was removed on a rotary evaporator, and the residue was dissolved in 500 mL of water. The solution was washed with methylene chloride (discarded), acidified to pH 1 with 6N HCl, and extracted with methylene chloride. The combined extracts were washed with water and dried over Na₂SO₄. The solvent was removed on a rotary evaporator to give 70 g of the intermediate diketoester as an oil. Potassium hydroxide (128.8 g (2.3 mol)) was dissolved in 2.0 L of ethanol. To the solution was added 85.5 g (0.23 mol) of crude diketoester (from the above and a similar run on smaller scale) and the solution was heated to reflux for 3 h. The ethanol was removed on a rotary evaporator and to the residue was added 1200 mL of concentrated hydrochloric acid. The mixture was heated at 85° C. for 3 h. The bulk of the aqueous HCl was removed on a rotary evaporator, and the residue was dissolved in 500 mL of water, and made alkaline with sodium carbonate. The solution was washed (discarded) with 200 mL of methylene chloride, and the aqueous phase was acidified to pH 1 with 2N HCl. The mixture (gummy residue) was extracted with 3×300 mL of methylene chloride, and the combined extracts were washed with water and dried over Na₂SO₄. The solvent was removed on a rotary evaporator to give 60.0 g (87% yield) of (S)-5-[[oxo-1-(phenylmethyl)-2-pyrrolidinyl]methyl]-1,3-cyclohexanedione as a white solid, mp 159°-161° C. (ethyl acetate). ¹H NMR (CDCl₃) (9:1 keto:enol forms) δ 1.38 (ddd, 1H, J$_{vic}$=4 and 11 Hz, J=14 Hz, CH of CH₂), 1.60-2.71 (m, 10 H, 4 CH₂, CH of CH₂, CH), 3.37 (s, 10/9 H, CH₂ of keto), 3.46 (m, 1 H, NCH), 3.94 and 4.96 (AB, 8/9 H, $J_{gem}=15$ Hz, CH$_2$ of enol), 3.95 and 4.99 (AB, 10/9 H, $J_{gem}=15$ Hz, CH$_2$ of keto), 5.45 (s, 4/9 H, =CH of enol), 7.19 (br d, 2H, $J_{ortho}=7$ Hz, arom), 7.30 (t, 1H, $J_{ortho}=7$ Hz, arom), 7.32 (t, 2H, $J_{ortho}=7$ Hz, arom). IR (CHCl$_3$) 1730, 1710, 1600, 702 cm$^{-1}$. MS (EI) m/e 299 (M+). $[\alpha]^{25}_D= +44.97°$ (c 1.04, methanol). Anal. Calcd for C$_{18}$H$_{21}$NO$_3$: C, 72.22; H, 7.07; N, 4.68. Found C, 72.39; H, 7.39; N, 4.72.

EXAMPLE 9

(5S,1R)-5-[(3-Ethoxy-5-oxo-3-cyclohexen-1-yl)methyl]-1-(phenylmethyl)-2-pyrrolidinone and (5s,1)-5-[(3-ethoxy-5-oxo-3-cyclohexen-1-yl)methyl]-1-(phenylmethyl)-2-pyrrolidinone A solution of (S)-5-[[oxo-1-(phenylmethyl)-2-pyrrolidinyl]methyl]-1,3-cyclohexanedione (60 g, 0.20 mol) and p-toluenesulfonic acid monohydrate (3.8 g, 0.02 mol) in 600 mL of ethanol and 1200 mL of toluene was stirred and refluxed for 1.5 h. The solvent was removed on a rotary evaporator and the residue dissolved in methylene chloride. The methylene chloride solution was washed with saturated sodium bicarbonate solution, brine, and dried over Na$_2$SO$_4$. The solvent was removed on a rotary evaporator to give 57.6 g of a crude oil. The crude product was chromatographed on silica gel (800 g) eluting with 2-4% methanol in ethyl acetate to give a 1:1 mixture of diastereomeric products: (5S,1R)-5-[(3-ethoxy-5-oxo-3-cyclohexen-1-yl)methyl]-1-(phenylmethyl)-2-pyrrolidinone and (5s,1S)-5-[(3-ethoxy-5-oxo-3-cyclohexen-1-yl)methyl]-1-(phenylmethyl)-2-pyrrolidinone (37.5 g, 57% yield). A total of 25.5 g of mixture (from this and a similar preparation) was chromatographed using a Waters Prep 500 high pressure liquid chromatograph, eluting with 1:24:25 methanol:ethyl acetate:hexane, and recovering and re-chromatographing the mixed fractions. A total of 24.3 g (25.0% yield) of the more polar diastereomer, (5S,1R)-5-[(3-ethoxy-5-oxo-3-cyclohexen-1-yl)methyl]-1-(phenylmethyl)-2-pyrrolidinone, and a total of 23.9 g (24.6% yield) of the less polar diastereomer, (5S,1S)-5-[(3-ethoxy-5-oxo-3-cyclohexen-1-yl)methyl]-1-(phenylmethyl)-2-pyrrolidinone was obtained.

For (5S,1R)-5-[(3-ethoxy-5-oxo-3-cyclohexen-1-yl)methyl]-1-(phenylmethyl)-2-pyrrolidinone: mp 99°-102° C. TLC (ethyl acetate:methanol 95:5) R$_f$=0.4. $[\alpha]^{25}_D= +3.08°$ (methanol, c=1.0) $^1$H NMR (CDCl$_3$) δ 1.35 (t, J=6 Hz, 3 H, CH$_3$), 1.50-2.50 (m, 11 H, CH$_2$ and CH), 3.46 (m, 1 H, CHN), 3.90 (q, J=6 Hz, 2 H, CH$_2$CH$_3$), 3.95 and 5.05 (AB, $J_{gem}=15$ Hz, 2 H, CH$_2$Ph), 5.35 (s, 1 H, vinyl H), 7.24-7.34 (m, 5 H, phenyl). MS (EI) m/e 327 (M+). IR (CHCl$_3$) 1672 cm$^{-1}$ (C=O). Anal. Calcd for C$_{20}$H$_{25}$NO$_3$: C, 73.37; H, 7.70; N, 4.28. Found: C, 73.18; H, 7.59; N, 4.24.

For (5S,1S)-5-[(3-ethoxy-5-oxo-3-cyclohexen-1-yl)methyl]-1-(phenylmethyl)-2-pyrrolidinone: mp 108°-110° C. TLC (ethyl acetate:methanol 95:5), R$_f$=0.5. $[\alpha]^{25}_D= +15.85°$ (methanol, c=1.0) $^1$H NMR (CDCl$_3$) δ 1.35 (t, J=6Hz, 3 H, CH$_3$), 1.50-2.50 (m, 11 H, CH$_2$ and CH), 3.46 (m, 1H, CHN), 3.90 (q, J=6 Hz, 2 H, CH$_2$CH$_3$), 3.96 and 5.00 (AB, $J_{gem}=15$ Hz, 2 H, CH$_2$Ph), 5.35 (s, 1 H, vinyl H), 7.24-7.34 (m, 5 H, phenyl). MS (EI) m/e 327 (M+). IR (CHCl$_3$) 1672 cm$^{-1}$ (C=O). Anal. Calcd for C$_{20}$H$_{25}$NO$_3$: C, 73.37; H, 7.70; N, 4.28. Found: C, 73.02; H, 7.72; N, 4.40.

In a similar sequence, the diastereomeric mixture was prepared as a racemate, starting from racemic 1-(phenylmethyl)-5-(2-propenyl)-2-pyrrolidinone. The less polar diastereomer was recrystallized from ethyl acetate-hexane to give crystals suitable for X-ray analysis, mp 112°-113° C. The single crystal analysis established that the less polar diastereomer is (5S*,1S*)-5-[(3-ethoxy-5-oxo-3-cyclohexen-1-yl)methyl]-1-(phenylmethyl)-2-pyrrolidinone (R factor 0.055, wR=0.050).

EXAMPLE 10

Recycling of (5S,1R)-5-[(3-ethoxy-5-oxo-3-cyclohexen-1-yl)methyl]-1-(phenylmethyl)-2-pyrrolidinone and (5S,1S)-5-[(3-ethoxy-5-oxo-3-cyclohexen-1-yl)methyl]-1-(phenylmethyl)-2-pyrrolidinone A mixture of (5S,1R)-5-[(3-ethoxy-5-oxo-3-cyclohexen-1-yl)methyl]-1-(phenylmethyl)-2-pyrrolidinone and (5S,1S)-5-[(3ethoxy-5-oxo-3-cyclohexen-1-yl)methyl[-1-(phenylmethyl)-2-pyrrolidinone (150 mg, 0.46 mmol) in 10 mL of tetrahydrofuran was treated with 2 mL of 2N HCl and stirred at room temperature for 2 h, then refluxed for 1 h. The solvent was removed on a rotary evaporator and the residue was extracted with methylene chloride. The combined extracts were dried over Na$_2$SO$_4$ and evaporated to give 130 mg of (S)-5-[[oxo-1-(phenylmethyl)-2-pyrrolidinyl]methyl]-1,3-cyclohexanedione, mp 159°-161° C. (ethyl acetate), which was identical in all respects to that obtained in the synthesis from (E)-4-[2(S)-5-oxo-1-(phenylmethyl)-2-pyrrolidinyl]-2-butenoic acid, ethyl ester.

EXAMPLE 11

(5S,1R)-5-[(3-methyl-5-oxo-3-cyclohexen-1-yl)methyl]-1-(phenylmethyl)-2-pyrrolidinone To a solution of (5S,1R)-5-[(3-ethoxy-5-oxo-3-cyclohexen-1-yl)methyl]-1-(phenylmethyl)-2-pyrrolidinone (3.94 g, 12.0 mmol) in 150 ml of 1:1 tetrahydrofuran:ether was added a solution of methyllithium (41 mL, 1.4M in ether, 57.4 mmol) at −78° C. over 10 min. The mixture was stirred for 30 min at −78° C. and quenched by the addition of 50 mL of 50% aqueous acetic acid. The mixture was allowed to warm to room temperature and was extracted with methylene chloride. The combined extracts were washed with saturated sodium bicarbonate, dried over Na$_2$SO$_4$ and concentrated on a rotary evaporator to give 4.05 g of a crude oil. Chromatography of the crude product on silica gel (100 g) eluting with 1% methanol in ethyl acetate afforded 1.85 g (52% yield) of (5S,1R)-5-[(3-methyl-5-oxo-3-cyclohexen-1-yl)methyl]-1-(phenylmethyl)-2-pyrrolidinone as an oil. A sample was evaporatively distilled at 200°-210° C./0.05 torr for analysis. $^1$H NMR (CDCl$_3$) δ 1.94 (s, 3 H, CH$_3$), 1.35-2.55 (m, 11 H, CH$_2$ and CH), 3.45 (m, 1 H, NCH), 3.95 and 4.98 (AB, $J_{gem}=15$ Hz, 2 H, CH$_2$Ph), 3.87 (s, 1 H, vinyl H), 7.50 (m, 5 H, phenyl). MS (EI) m/e 297 (M+). $[\alpha]^{25}_D= +59.86°$(c 0.2155 in methanol). CD (ethanol) 326 ([Θ]=−1425, max), 283 ([Θ]=−42, min), 238 ([Θ]=+13,620, infl), 218 ([Θ]=+50,100, max), 212 nm ([Θ]=+39,820°, min). Anal. Calcd for C$_{19}$H$_{23}$NO$_2$: C, 76.74; H, 7.80; N, 4.71. Found: C, 74.55; H, 7.53, N, 7.41.

EXAMPLE 12

[5S-(5S)]-3-Methyl-5-[[5-oxo-1-(phenylmethyl)-2-pyrrolidinyl]methyl]-2-cyclohexen-1-ylideneacetic acid ethyl ester To a solution of diisopropylamine (1.50 g, 14.8 mmol) in 20 mL of tetrahydrofuran at −30° C. was added n-butyllithium (6.0 mL, 2.5M, 15.0 mmol) and the solution was stirred for 30 min. at −30° C. and then cooled to −50° C. A solution of ethyl trimethylsilylacetate (2.40 g, 15.0 mmol) in 20 mL of tetrahydrofuran was added over 10 min and the solution was stirred at −40° to −50° C. for 1 h. A solution of (5S,1R)-5-[(3-methyl-5-oxo-3-cyclohexen-1-yl)methyl[-1-(phenylmethyl)-2-pyrrolidinone (1.85 g, 6.23 mmol) in 20 mL of tetrahydrofuran was added at −50° C. over 10 min, and the solution was allowed to warm to −20° C. over 30 min. The cold solution was poured into ice water and the mixture extracted with methylene chloride. The combined extracts were washed with brine, dried over MgSO$_4$ and the solvent was removed on a rotary evaporator to give 2.55 g of crude product as an oil. Chromatography on silica gel (100 g) eluting with 1% methanol in ethyl acetate afforded 1.78 g of [5S-(5S)]-3-methyl-5-[[5-oxo-1-(phenylmethyl)-2-pyrrolidinyl]methyl]-2-cyclohexen-1-ylideneacetic acid ethyl ester (3:2 mixture of Z/E isomers) as an oil. A sample was evaporatively distilled at 200°–210° C./0.05 torr for analysis. $^1$H NMR (CDCl$_3$) δ 1.25 (2t (Z/E), 3H, OCH$_2$CH$_3$), 1.60 and 1.70 (2s (Z/E), CH$_3$), 1.20–2.50 (m, 12 H, C$\overline{\text{H}}_2$ and CH), 3.45 and 3.58 (2m, (Z/E), NCH), 3.90, 5.00 and 3.99, 4.90 (2AB, (Z/E), J$_{gem}$=15 Hz, 2 H, CH$_2$Ph), 4.08 and 4.15 (2q, J=6 Hz, 2 H, OCH$_2$CH$_3$), 5.30 and 5.50 (2s (Z/E), 1 H, ring vinyl H), 5.90 and 7.25 (2s, (Z/E), 1 H, chain vinyl H), 7.20–7.4 (m, 5 H, phenyl). MS (EI) m/e 367 (M+). CD (ethanol) 276 ([Θ]=+13,125,max), 232 ([Θ]=+1,495, max), 217 ([Θ]=+33,643, max), 213 ([Θ]=+30,321, min), 198 nm ([Θ]=+45,690°, max) Anal. Calcd for C$_{23}$H$_{29}$NO$_3$: C, 75.17; H, 7.95; N, 3.81. Found: C, 75.17; H, 7.99; N, 3.66.

EXAMPLE 13

[1R,3R,5S,5(2S)]-3-Methyl-5-[[5-oxo-1-(phenylmethyl)-2-pyrrolidinyl]methyl]cyclohexaneacetic acid ethyl ester

[5S-(5S)]-3-methyl-5-[[5-oxo-1-(phenylmethyl)-2-pyrrolidinyl]methyl]-2-cyclohexen-1-ylideneacetic acid ethyl ester (1.72 g, 4.67 mmol) was hydrogenated in 80 mL of ethanol at 50 psi over 10% palladium on carbon for 5 h. The catalyst was filtered off, and the solvent was removed on a rotary evaporator to give 1.47 g of [[1R,3R,5S,5(2S)]-3-methyl-5-[[5-oxo-1-(phenylmethyl)-2-pyrrolidinyl]methyl]cyclohexaneacetic acid ethyl ester containing ca. 15% of two other diastereomers by NMR. A sample was evaporatively distilled at 200°–210° C./0.25 torr for analysis. $^1$H NMR (CDCl$_3$) δ 0.4 (q, J=10 Hz, 1H, axial CH), 0.55 (m, 2H, 2 axial CH), 0.84 (d,J=6.6 Hz, 0.45H, CH$_3$ of minor diastereomer), 0.86 (d,J=6.6 Hz, 2.1H, CH$_3$ of major diastereomer), 0.96 (d, J=6.6 Hz, 0.45H, CH$_3$ of minor diastereomer), 1.20 (t,J=6 Hz, 3H, OCH$_2$CH$_3$), 1.20–2.50 (m,14H, CH$_2$ and CH), 3.45 (m, 1H, CH$\overline{\text{N}}$), 4.10 (q,J=6 Hz, OCH$_2$CH$_3$), 3.95 and 4.96 (AB,J$_{gem}$=15 Hz, 2H, CH$_2$Ph), 7.20–7.35 (m, 5H, phenyl). MS (EI) m/e 371 (M+). CD (ethanol) 264 ([Θ]=+118, max), 261 ([Θ]=+65, min), 258 ([Θ]=+191, max), 254 ([Θ]=+121, min), 233 ([Θ]=−1032, max), 217 ([Θ]=+32,475, max), 211 ([Θ]=+28,070, min), 195 nm ([Θ]=+46,787°, max). Anal. Calcd for C$_{23}$H$_{29}$NO$_3$: C,75.17;H, 7.95; N,3.81. Found: C,75.17;H,7.99;N,3.66.

Example 14

[1R,3R,5S,5(2S)]-3-Methyl-5-[[5-oxo-1-(phenylmethyl)-2-pyrrolidinyl]methyl]cyclohexaneacetamide A mixture of [[1R,3R,5S,5(2S)]-3-methyl-5-[[5-oxo-1-(phenylmethyl)-2-pyrrolidinyl]methyl]cyclohexaneacetic acid ethyl ester (1.4 g, 3.77 mmol) and potassium hydroxide (2.0 g, 35 mmol) in 40 mL of ethanol was heated to reflux for 30 min, cooled, and the solvent was removed on a rotary evaporator. The residue was dissolved in water and acidified to pH 1 with 2N HCl and extracted with methylene chloride. The combined extracts were washed with brine, dried over Na$_2$SO$_4$ and evaporated to give 1.31 g of [1R,3R,5S,5(2S)]-3-Methyl-5-[[5-oxo-1-(phenylmethyl)-2-pyrrolidinyl]methyl]cyclohexaneacetic acid (1.31 g). The crude acid (1.31 g, 3.82 mmol) was dissolved in 15 mL of chloroform and cooled to −30° C. To the solution was added dropwise ethyl chloroformate (2.06 g, 19.1 mmol) in 15 mL of chloroform followed by triethylamine (1.93 g, 19.1 mmol) in 10 mL of chloroform. After the addition was complete, the mixture was allowed to warm over 1 h to 0° C. Ammonia was then bubbled into the solution for 20 min. The mixture was stirred for 1 h at 0° C. and then allowed to warm to room temperature. The precipitate (NH$_4$Cl) was filtered off and the filtrate was washed with 2 N HCl, saturated sodium bicarbonate, and brine, and dried over Na$_2$SO$_4$. The solvent was removed on a rotary evaporator to give 2.05 g of crude [1R,3R,5S,5(2S)]-3-methyl-5-[[5-oxo-1-(phenylmethyl)-2-pyrrolidinyl]methyl]cyclohexaneacetamide which was chromatographed on silica gel (80 g) eluting with 5% methanol in ethyl acetate to give 1.05 g of chromatographed acetamide. Recrystallization from tetrahydrofuran:ether 1:3 at −20° C., then from tetrahydrofuran:ether 1:2 at room temperature afforded 0.23 g of [1R,3R,5S,5(2S)]-3-methyl-5-[[5-oxo-1-(phenylmethyl)-2-pyrrolidinyl]methyl]cyclohexaneacetamide as a single diastereomer, mp 90°–92° C. An additional 0.35 g was obtained from the mother liquors by HPLC. (Waters Prep 500, 4% methanol, 48% ethyl acetate, 48% hexane). $^1$H NMR (CDCl$_3$) δ 0.4 (q,J=10 Hz, 1H, axial ring CH), 0.5–0.62 (m, 2H, axial ring CH), 0.86 (d,J=6.5 Hz, 3H, CH$_3$), 1.15–2.55 (m, 14H, CH$_2$ and CH), 3.47 (m, 1 H, NCH), 3.94 and 4.97 (AB,J$_{gem}$=15 Hz, CH$_2$Ph), 5.30 (br d,J=15 Hz, 2 H, CONH$_2$), 7.20–7.35 (m, 5 H, phenyl). MS (EI): m/e 342 (M+). HRMS (FAB): Calcd for C$_{21}$H$_{30}$N$_2$O$_2$ (M+H) 342.2307. Obsd (M+H) 342.2297. CD (ethanol) 264 ([Θ]=+115, max), 261 ([Θ]=+52, min), 258 ([Θ]=+190, max), 255 ([Θ]=+107, min), 252 ([Θ]=+164, max), 233 ([Θ]=−1,850, max), 216 ([Θ]=+41,667, max), 211 ([Θ]=+36,980, min), 196 nm ([Θ]=+57812°, max). Anal. Calcd for C$_{21}$H$_{30}$N$_2$O$_2$: C, 72.50; H, 8.69; N, 8.05. Found C, 72.27; H, 8.91; N, 8.06.

EXAMPLE 15

[1R,3R,5S,5(2S)]-3-Methyl-5-[[5-oxo-2-pyrrolidinyl]methyl]cyclohexaneacetamide

A solution of [1R,3R,5S,5(2S)]-3-methyl-5-[[5-oxo-1-(phenylmethyl)-2-pyrrolidinyl]methyl]cyclohexaneacetamide (0.58 g, 1.70 mmol) in 10 mL of tetrahydrofuran was placed in a flask equipped with a Dry Ice condenser, and ammonia (10 mL) was condensed into the solution. To the solution at reflux was added sodium metal (0.39 g, 17.0 mg-atom) in small pieces. The resulting blue solution was stirred for 30 min and was quenched by the addition of solid ammonium chloride. The Dry Ice condenser was removed, and the ammonia was allowed to evaporate. The mixture was then diluted with methylene chloride and filtered. The filtrate was concentrated on a rotary evaporator and the residue was chromatographed on silica gel (15 g) eluting with 5–10% methanol in ethyl acetate to give 0.275 g of [1R,3R,5S,5(2S)]-3-methyl-5-[[5-oxo-2-pyrrolidinyl]methyl]cyclohexaneacetamide as a white solid, mp 190°–192° C. (ethanol). $^1$H NMR (CDCl$_3$) δ 0.4–0.6 (m, 3 H, axial ring H), 0.90 (d,J=6 Hz, 3 H, CH$_3$), 1.3–2.20 (m, 14 H, CH$_2$ and CH), 3.77 (m, 1 H, CHN), 5.45, and 5.80 (2s, 2 H, CONH$_2$), 6.40 (s, 1 H, NH). IR (CHCl$_3$) 1688 cm$^{-1}$. MS (EI) m/e 252 (M+). CD (ethanol) 215 ([Θ]= −11.120, max), 195 ([Θ]= +21,685, max). Anal. Calcd for C$_{14}$H$_{24}$N$_2$O$_2$: C, 66.63; H, 9.59;, N, 11.10. Found: C, 66.31; H, 9.56; N, 11.06.

Crystal structure determination of [1R,3R,5S,5(2S)]-3-methyl-5-[[5-oxo-2-pyrrolidinyl]methyl]cyclohexaneacetamide.

Intensity data were measured on a Hilger-Watts diffractometer (Ni-filtered, Cu Kα radiation, θ-2θ scans, pulse-height discrimination). The size of the crystal used for data collection was approximately 0.12×0.15×0.85 mm; the data were not corrected for absorption. Of the 1106 independent reflections for θ<57°, 1063 were considered to be observed [I>2.5σ (I)].

The structure was solved by a multiple-solution procedure (G. Germain, P. Main, and M. M. Woolfson, *Acta Cryst.* 1971, A27, 368) and was refined by a full-matrix least squares. In the final refinement, anisotropic thermal parameters were used for the nonhydrogen atoms and isotropic temperature factors were used for structure factor calculations but their parameters were not refined. The final discrepancy indices are R=0.038 and wR=0.043 for the 1063 observed reflections. The final difference map has no peaks greater than ±0.2 e A$^{-3}$. The crystal data were as follows:

| Crystal system | monoclinic |
|---|---|
| Space group | P2$_1$ |
| a | 8.620(1) Å |
| b | 8.229(2) Å |
| c | 11.424(2) Å |
| β | 111.50(1)° |
| Z | 2 |
| d$_{calcd}$ | 1.111 g cm$^{-3}$ |
| μ(Cu K$_α$) | 6.0 cm$^{-1}$ |

EXAMPLE 16

[5S-5(2S)]-3-Oxo-5-[[5-oxo-1-(phenylmethyl)-2-pyrrolidinyl]methyl]-1-cyclohexene-1-acetic acid ethyl ester To a solution of diisopropylamine (0.75 g, 7.5 mmol) in 15 mL of ether was added at −50° C. a solution of n-butyllithium (3.0 mL, 2.5M, in hexane, 7.5 mmol) and the mixture was stirred for 30 min at −20° to −30° C. A solution of ethyl trimethylsilylacetate (1.20 g, 7.5 mmol) in 15 mL of ether was added at −50° C. and the mixture was stirred at −30° to −40° C. for 1 h. To the solution was added (5S,1S)-5-[(3-ethoxy-5-oxo-3-cyclohexen-1-yl)methyl]-1-(phenylmethyl)-2-pyrrolidinone (1.0 g, 3.06 mmol) in 15 mL of dry tetrahydrofuran at −50° C. Following the addition, the mixture was allowed to warm slowly over 1 h to 0° C., and was poured onto ice water. The mixture was extracted with methylene chloride and the solvent was removed on a rotary evaporator. The residual material was dissolved in 15 mL of tetrahydrofuran and 15 mL of 12N HCl was added and the mixture was stirred for 30 min at room temperature. The mixture was extracted with methylene chloride and the extracts were washed with saturated sodium bicarbonate, brine, and dried over Na$_2$SO$_4$. The solvent was removed on a rotary evaporator to give 1.1 g of crude [5S-5(S)]-3-oxo-5-[[5-oxo-1-(phenylmethyl)-2-pyrrolidinyl]methyl]-1-cyclohexene-1-acetic acid ethyl ester which was chromatographed on silica gel (30 g) eluting with 1% methanol in ethyl acetate to give 0.8 g of [5S-5(2S)]-3-oxo-5-[[5-oxo-1-(phenylmethyl)-2-pyrrolidinyl]methyl]-1-cyclohexene-1-acetic acid ethyl ester. A sample was evaporatively distilled at 230°–240° C./0.25 torr for analysis. $^1$H NMR (CDCl$_3$) δ 1.26 (t,J=7 Hz, CH$_3$), 1.25–2.60 (m, 11 H, CH$_2$ and CH), 3.14 and 3.15 (AB,J$_{gem}$=15 Hz, 2 H, CH$_2$CO), 3.47 (m, 1 H, NCH), 3.97 and 5.00 (AB,-J$_{gem}$=15 Hz, 2 H, CH$_2$Ph), 4.15 (q,J=7 Hz, 2 H, OCH$_2$), 7.20–7.40 (m, 5 H, phenyl). MS (EI) m/e 369 (M+). Anal. Calcd for C$_{22}$H$_{27}$NO$_4$: C, 71.52; H, 7.37; N, 3.79. Found: C, 70.75; H, 7.42; N, 3.62.

EXAMPLE 17

[1S,5S,5(2S)]-3-Oxo-5-[[5-oxo-1-(phenylmethyl)-2-pyrrolidinyl]methyl]-cyclohexaneacetic acid ethyl ester A solution of [5S-5(2S)]-3-oxo-5-[[5-oxo-1-(phenylmethyl)-2-pyrrolidinyl]methyl]-1-cyclohexene-1-acetic acid ethyl ester (0.75 g, 2.03 mmol) in 30 mL of ethanol was hydrogenated over 10% palladium on carbon (0.25 g) at 50 psi for 3 h. The mixture was filtered to remove the catalyst, and the solvent was removed on a rotary evaporator. The crude product was chromatographed on silica gel, eluting with 1% methanol in ethyl acetate to give 0.6 g of [1S,5S,5(2S)]-3-oxo-5-[[5-oxo-1-(phenylmethyl)-2-pyrrolidinyl]methyl]cyclohexaneacetic acid ethyl ester. A sample was evaporatively distilled at 220°–240° C./0.25 torr for for analysis. $^1$H NMR (CDCl$_3$) δ 0.95 (m, 1 H, axial ring H), 1.25 (t,J=7 Hz, 3 H, CH$_3$), 1.6–2.6 (m, 13 H, CH$_2$ and CH), 3.45 (m, 1 H, NCH), 3.97 and 4.98 (AB,J$_{gem}$=15 Hz, 2 H, CH$_2$Ph), 4.12 (q,J=7 Hz, 2 H, OCH$_2$), 7.20–7.40 (m, 5H, phenyl). MS (EI) m/e 371 (M+). [α]$^{25}$$_D$= +16.88° (c 0.9359 in methanol). Anal. Calcd for C$_{22}$H$_{29}$NO$_4$: C, 71.13; H, 7.87; N, 3.77. Found: C, 71.08; H, 7.72; N, 3.75.

EXAMPLE 18

[2-[(Phenylmethyl)amino]ethenyl]phosphonic acid diethyl ester

Diethyl phosphonoacetaldehyde diethyl acetal (12.0 g, 0.047 mol) in 50 mL of 2.5% HCl in water was heated to reflux for 30 min. The solution was cooled to room temperature, saturated with sodium chloride, and extracted with methylene chloride. The combined extracts were washed with a 1:1 mixture of brine and saturated sodium bicarbonate and dried over sodium sulfate. The solvent was removed on a rotary evaporator and the residue (8.0 g) of diethylphosphonoacetaldehyde was used without purification. The crude diethylphosphonoacetaldehyde was dissolved in 25 mL of methanol and benzylamine (5.4 g, 0.05 mol) was added. The mixture was stirred for 1 h, the solvent was removed on a rotary evaporator, and the residue was evaporatively distilled at 90°–92° C./0.5 torr to give [2-[(phenylmethyl)amino]ethenyl]phosphonic acid diethyl ester (6.60 g) as an oil. $^1$H NMR (CDCl$_3$) δ 1.28 (t,J=7 Hz, 6 H, CH$_3$'s), 3.95–4.30 (m, 7 H, CH$_2$'s and vinyl H), 4.8 (br s, 1 H, NH), 7.20–7.42 (m, 6 H, phenyl and vinyl H).

EXAMPLE 19

[1S,5R,5(2S)]-5-[[5-Oxo-1-(phenylmethyl)-2-pyrrolidinyl]methyl]-3-[[(phenylmethyl)imino]ethylidene]-cyclohexaneacetic acid ethyl ester To a solution of diisopropylamine (1.40 g, 14.0 mmol) in 15 mL of ether was added a solution of n-butyllithium in hexane (5.6 mL, 2.5M, 14.0 mmol) at −30° C. The mixture was stirred for 30 min at −30° C. and a solution of [2-[(phenylmethyl)amino]ethenyl]-phosphonic acid diethyl ester (3.76 g, 14.0 mmol) in 10 mL of tetrahydrofuran was added at −40° C. The solution was stirred for 1 h at −15° to −20° C. and then cooled to −40° C. To the solution was added a solution of [1S,5S,5(2S)]-3-oxo-5-[[5-oxo-1-(phenylmethyl)-2-pyrrolidinyl]methyl]-cyclohexaneacetic acid ethyl ester (1.30 g, 3.80 mmol) in 10 mL of tetrahydrofuran at −40° C. The mixture was stirred and allowed to warm slowly to 0° C., then poured into ice water and extracted with methylene chloride. The extracts were washed with brine and dried over Na$_2$SO$_4$ and the solvent was removed on a rotary evaporator. The crude product was chromatographed on silica gel, eluting with 1% methanol in ethyl acetate to give 0.72 g of [1S,3R,5(2S),5S]-3-[[5-oxo-1-(phenylmethyl)-2-pyrrolidinyl]methyl]-5-[[(phenylmethyl)imino]ethylidene]cyclohexaneacetic acid ethyl ester, which also contained ca. 30–50% of the corresponding aldehyde, [1S,5R,5(2S)]-3-oxoethylidene-5-[[5-oxo-1-(phenylmethyl)-2-pyrrolidinyl]-methyl]cyclohexaneacetic acid ethyl ester. $^1$H NMR (CDCl$_3$) δ 0.65–1.00 (m, 2 H, axial ring H), 1.15–1.35 (2t, 3 H, CH$_3$), 3.50 (m, 1 H, NCH), 3.95–4.20 (m, 4, CH$_2$CO), 4.00, and 5.00 (AB, J$_{gem}$=15 Hz, 2 H, CH$_2$Ph), 5.87 and 6.05 (2 br d, 1 H, vinyl H), 7.20–7.40, (m, 6 H, phenyl and imine H), 8.34 (br d, ca. 0.5 H, aldehyde vinyl H), 9.96 (2 d, J=7.5 Hz, CHO (E/Z)). The chromatographed imine/aldehyde mixture was used directly in the following step.

EXAMPLE 20

[1S,5R,5(2S)]-5-[[5-Oxo-1-(phenylmethyl)-2-pyrrolidinyl]methyl]-3-[[1-(phenylmethyl)-1H-imidazol-5-yl]methylene]cyclohexaneacetic acid ethyl ester To a solution of the imine/aldehyde mixture from Example 19 (1.315 g, 2.70 mmol) in 40 mL of methanol was added benzylamine (2.75 g, 25.7 mmol) and the mixture was stirred for 1 h at room temperature over 4A molecular sieves (ca. 1.5 g). The mixture was filtered and concentrated on a rotary evaporator to remove the bulk of the methanol, then diluted with methylene chloride. The solution was dried over anhydrous MgSO$_4$ and the methanol solvent was removed on a rotary evaporator The residue, consisting of the imine and benzylamine, was redissolved in 45 mL of methanol, and 4-toluenesulfonylmethylisocyanide (TOSMIC) (2.65 g, 13.6 mmol) was added. The solution was stirred at room temperature overnight, and was concentrated on a rotary evaporator, then at 35° C./1.0 torr. The residue was chromatographed on silica gel eluting with 2% methanol in methylene chloride to afford 0.98 g of [1S,5R,5(2S)-3-[[5-oxo-1-(phenylmethyl)-2-pyrrolidinyl]-methyl]-5-[[1-(phenylmethyl)-1H-imidazol-5-yl]methylene]cyclohexaneacetic acid ethyl ester. $^1$H NMR (CDCl$_3$) δ 0.6–0.7 (m, 1 H, axial ring H), 1.23 (t, J=6 Hz, 3 H, OCH$_3$), 3.42 (br s, 1 H, NCH), 5.07 (s, 2 H, imidazole-NCH$_2$Ph), 5.78 (s, 1 H, vinyl H), 6.92 and 7.54 (2 s, 2 H, imidazole-H's), 7.0–7.4 (m, 10 H, phenyl).

EXAMPLE 21

[1S,5R,5(2S)-5-[[5-Oxo-1-(phenylmethyl)-2-pyrrolidinyl]methyl]-3-[[1-(phenylmethyl)-1H-imidazol-5-yl]methylene]cyclohexaneacetamide

[1S,5R,5(2S)-5-[[5-oxo-1-(phenylmethyl)-2-pyrrolidinyl]methyl]-3-[[1-(phenylmethyl)-1H-imidazol-5-yl]methylene]cyclohexaneacetic acid ethyl ester (0.98 g, 1.86 mmol) was heated to 75° C. in 16 mL of ethanol with potassium hydroxide (0.56 g, 10.0 mmol). The mixture was concentrated on a rotary evaporator, diluted with 15 mL of water, and acidified to pH 3.5 with 2N HCl. The mixture was extracted with methylene chloride, and the combined extracts were dried over Na$_2$SO$_4$ and the solvent was removed on a rotary evaporator to give [1S,5R,5(2S)-5-[[5-oxo-1-(phenylmethyl)-2-pyrrolidinyl]methyl]-3-[[1-(phenylmethyl)-1H-imidazol-5-yl]methylene]cyclohexaneacetic acid. The crude acid was dissolved in 50 mL of chloroform, cooled to −30° C., and treated with 0.85 g, 10.0 mmol) of ethyl chloroformate, followed by triethylamine (1.0 g, 10.0 mmol). The mixture was stirred and allowed to warm slowly to 0° C., and was maintained at 0° C. while ammonia was bubbled into the solution for 20 min. The white suspension was stirred for 1 h at 0° C., then allowed to warm to room temperature. The mixture was filtered to remove the ammonium chloride precipitate, and concentrated on a rotary evaporator. The residue was chromatographed on silica gel (dry column), eluting with the lower phase of a mixture prepared by shaking chloroform, methanol, water, and acetic acid together in a 9:3:1:0.6 ratio. The chromatography fractions were washed with saturated sodium bicarbonate and dried over Na$_2$SO$_4$ prior to evaporation to give 0.7 g of [1S,5R,5(2S)]-5-[[5-oxo-1-(phenylmethyl)-2-pyrrolidinyl]methyl]-5-[[1-(phenylmethyl)-1H-imidazol-5-yl]methylene]cyclohexaneacetamide. $^1$H NMR (CDCl$_3$) δ 0.58–0.80 (m, 1 H, axial ring H), 2.74 (br d,J=11 Hz, CH of CH$_2$), 3.42 (br s, 1 H, NCH), 3.96 and 4.96 (AB,J$_{gem}$=15 Hz, 2 H, CH$_2$Ph on lactam), 5.04 (s, 2 H, NCH$_2$Ph on imidazole), 5.37 (br d, J=8 Hz, 2 H, CONH$_2$), 5.78 (s, 1 H, vinyl H), 6.91 and 7.46 (2 s, 2 H, imidazole-H's), 6.99–7.40 (m, 10 H, phenyls).

EXAMPLE 22

(a)

[1S,3RS,5(2S),5S]-5-[[5-Oxo-1-(phenylmethyl)-2-pyrrolidinyl]methyl]-3-[[1-(phenylmethyl)-1H-imidazol-5-yl-]methyl]cyclohexaneacetamide A solution of [1S,5R,5(2S)]-5-[[5-oxo-1(phenylmethyl)-2-pyrrolidinyl]methyl]-3-[[1-(phenylmethyl)-1H-imidazol-5-yl]methylene]cyclohexaneacetamide (0.67 g, 1.35 mmol) in 30 mL of ethanol was hydrogenated at 1 atm over 10% palladium on carbon (0.15 g) overnight. The mixture was filtered and the solvent was removed on a rotary evaporator. The crude product was chromatographed on silica gel (dry column), eluting with the lower phase of a mixture prepared by shaking chloroform, methanol, water, and acetic acid together in a 9:3:1:0.6 ratio. The chromatography fractions were washed with saturated sodium bicarbonate and dried over Na$_2$SO$_4$ prior to evaporation to give 0.31 g of [1S,3RS,5(2S),5S]-5-[[5-oxo-1-(phenylmethyl)-2-pyrrolidinyl]methyl]-3-[[1-(phenylmethyl)-1H-imidazol-5-yl]methyl]cyclohexaneacetamide, together with 0.21 g of recovered starting material. Rehydrogenation of the recovered material gave an additional 0.124 g (70% yield) of [1S,3RS,5(2S),5S]-5-[[5-oxo-1-(phenylmethyl)-2-pyrrolidinyl]methyl]-3-[[1-(phenylmethyl)-1H-imidazol-5-yl]methyl]cyclohexaneacetamide. $^1$H NMR (CD$_3$OD) δ 0.15–0.32 (m, 1 H, axial ring H), 3.42 (br s, 1 H, NCH), 3.92 and 4.92 (AB, J$_{gem}$=15 Hz, 2 H CH$_2$Ph on lactam), 5.05 (s, 2 H, CH$_2$Ph on imidazole), 5.40 (d, J=12 Hz, 2 H, CONH$_2$), 6.80 and 7.48 (2s, 2 H, imidazole H's), 7.00–7.40 (m, 10 H, phenyls). MS (EI) 498 (M+). HRMS (FAB): Calcd for C$_{31}$H$_{38}$N$_4$O$_2$ (M+H) 499.3073. Obsd (M+H) 499.3103.CD (ethanol) 264 ([Θ]=−89, min), 261 ([Θ]=−232, min), 258 ([Θ]=−89, min), 254 ([Θ]=−232, max), 252 ([Θ]=−149, min), 241 ([Θ]=−1,429, max), 240 ([Θ]=−1,190, min), 233 ([Θ]=−2,619, max), 219 ([Θ]=+33,930°, max), 210 ([Θ]=+28,570°, min), 200 nm ([Θ]=+50,000°, max)

(b)

[1S,3R,5(2S),5S]-5-[[5-Oxo-1-(phenylmethyl)-2-pyrrolidinyl]methyl]-3-[[1-(phenylmethyl)-1H-imidazol-5-yl]methyl]cyclohexaneacetamide A sample of 985 mg of [1S,3RS,5(2S),5S]-5-[[5-oxo-1-(phenylmethyl)-2-pyrrolidinyl]methyl]-3-[[1-(phenylmethyl)-1H-imidazol-5-yl]methyl]cyclohexaneacetamide prepared as described in (a) was chromatographed on silica gel (250 g, 70–230 mesh) eluting with a mixture of CHCl$_3$, CH$_3$OH, and HOAc in a ratio of 7:2:0.1. The chromatography fractions were washed with saturated sodium bicarbonate and dried over Na$_2$SO$_4$ prior to evaporation. From the chromatography there was obtained 167 mg of the less polar diastereomer, [1S,3R,5(2S),5S]-5-[[5-oxo-1-(phenylmethyl)-2-pyrrolidinyl]methyl]-3-[[1-(phenylmethyl)-1H-imidazol-5-yl]methyl]cyclohexaneacetamide: mp 75° C. (softens above 63° C.). $^1$H NMR (CDCl$_3$) δ 0.36–0.41 (m, 1 H, axial ring H), 0.43–0.58 (m, 2 H, axial ring H), 3.42 (br s, 1 H, NCH), 3.91 and 4.93 (AB,J$_{gem}$=15 Hz, 2 H CH$_2$Ph on lactam), 5.03 (s, 2 H, CH$_2$Ph on imidazole), 5.30 (d, J=12 Hz, 2 H, CONH$_2$), 6.80 and 7.46 (2s, 2 H, imidazole H's), 7.00–7.40 (m, 10 H, phenyls). MS (EI) 498 (M+). HRMS (EI): Calcd for C$_{31}$H$_{38}$N$_4$O$_2$ (M+) 498.2995. Obsd (M+) 498.2990. CD (ethanol) 258 ([Θ]=+80, max), 233 ([Θ]=−2,960, max), 216 ([Θ]=+38,400°, max), 213 ([Θ]=+33,600°, max), 200 ([Θ]=+56,000°, max).

(c)

[1S,3S,5(2S),5S]-5-[[5-Oxo-1-(phenylmethyl)-2-pyrrolidinyl]methyl]-3-[[1-(phenylmethyl)-1H-imidazol-5-yl]methyl]cyclohexaneacetamide From the chromatography described in (b) there was also obtained 100 mg of the more polar diastereoisomer, [1S,3S5(2S),5S]-5-[[5-oxo-1-(phenylmethyl)-2-pyrrolidinyl]methyl]-3-[[1-(phenylmethyl)-1H-imidazol-5-yl]methyl]cyclohexaneacetamide: mp 72° C. (softens above 56° C.). $^1$H NMR (CDCl$_3$) δ 0.36–0.46 (m, 1 H, axial ring H), 1.00–1.15 (m, 3 H), 3.42 (br s, 1 H, NCH), 3.92 and 4.92 (AB, J$_{gem}$=15 Hz, 2 H CH$_2$Ph on lactam), 5.03 (s, 2 H, CH$_2$Ph on imidazole), 5.30 (br s, 2 H, CONH$_2$), 6.79 and 7.44 (2s, 2 H, imidazole H's), 7.00–7.40 (m, 10 H, phenyls). MS (EI) 498 (M+). HRMS (EI): Calcd for C$_{31}$H$_{38}$N$_4$O$_2$ (M+) 498.2995. Obsd (M+H) 498.2965. CD (ethanol) 258 ([Θ]=−56, min), 232 ([Θ]=−2,360, max), 216 ([Θ]=+36,800°, max), 213 ([Θ]=+34,400°, max), 202 ([Θ]=+57,600°, max). Mixed fractions totaled 580 mg, and could be rechromatographed to provide additional pure isomers.

EXAMPLE 23

(a)

[1S,3RS,5(2S),5S]-5-[[5-Oxo-1-(phenylmethyl)-2-pyrrolidinyl]methyl]-5-[(1H-imidazol-5-yl)methyl]cyclohexaneacetamide A solution of [1S,3RS,5(2S),5S]-5-[[5-oxo-1-(phenylmethyl)-2-pyrrolidinyl]methyl]-3-[[1-(phenylmethyl)-1H-imidazol-5yl]methyl]cyclohexaneacetamide (100 mg, 0.2 mmol) in 50 mL of methanol was reduced with 10 atm of hydrogen at 50° C. over 10% palladium on carbon for 9 h. The mixture was filtered, and the solvent was removed on a rotary evaporator. The residue was chromatographed on silica gel (5 g). eluting with the lower phase of a mixture prepared by shaking chloroform, methanol, water, and acetic acid together in a 9:3:1:0.6 ratio to give 0.043 g of [1S,3RS,5(2S),5S]-5-[[5-oxo-1-(phenylmethyl)-2-pyrrolidinyl]methyl]-3-[(1H-imidazol-5-yl)methyl]cyclohexaneacetamide as a solid, mp 94°–100° C. $^1$H NMR (CD$_3$OD) δ 0.40–2.60 (m, 19 H, CH and CH$_2$'s), 3.55 (m, 1 H, NCH), 4.08 and 4.80 (AB,J$_{gem}$=15 Hz, CH$_2$Ph), 6.80 (s, 1 H, imidazole ring H), 7.55 (s, 1 H, imidazole ring H), 7.20–7.40 (m, 5 H, phenyl). MS (EI) m/e 409 (M+). HRMS (FAB): Calcd for C$_{24}$H$_{32}$N$_4$O$_2$ (M+H) 409.2603. Obsd (M+H) 409.2623. CD (ethanol) 264 ([Θ]=+112, max), 262 ([Θ]=+64, min), 258 ([Θ]=+168, max), 254 ([Θ]=+104, min), 251 ([Θ]=+160, max), 232 ([Θ]=−1,440, max), 216 ([Θ]=+34,000, max), 212 ([Θ]=+30,000, min), 199 nm ([Θ]=+49,000°, max).

(b)

[1S,3R,5(2S),5S]-5-[[5-Oxo-1-(phenylmethyl)-2-pyrrolidinyl]methyl]-5-[(1H-imidazol-5-yl)methyl]cyclohexaneacetamide In the same manner as described in (a), reduction of the less polar diastereomer, [1S,3R,5(2S),5S]-5-[[5-oxo-1-(phenylmethyl)-2-pyrrolidinyl]methyl]-3-[[1-(phenylmethyl)-1H-imidazol-5-yl]methyl]cyclohexaneacetamide, afforded [1S,3R,5(2S),5S]-5-[[5-oxo-1-(phenylmethyl)-2-pyrrolidinyl]methyl]-3-[(1 H-imidazol-5-yl)methyl]cyclohexaneacetamide. $^1$H NMR (CDCl$_3$) δ 0.47–0.47 (m, 1 H, axial ring H), 0.56–0.68 (m, 2 H, axial ring H), 3.44 (m, 1 H, NCH), 3.92 and 4.95 (AB,J$_{gem}$=15 Hz, CH$_2$Ph), 5.32 and 5.41 (br s, 2 H, amide H) 6.74 (s, 1 H, imidazole ring H), 7.54 (s, 1 H, imidazole ring H), 7.18–7.35 (m, 5 H, phenyl). MS (EI) m/e 408 (M+). HRMS (EI): Calcd for C$_{24}$H$_{32}$N$_4$O$_2$ (M+) 408.2525. Obsd (M+) 408.2519. CD (ethanol) 233 ([Θ]=−1,660, max), 217 ([Θ]=−39,200, max), 211 ([Θ]=+34,400, min), 199 nm ([Θ]=+59,200°, max).

(c)

[1S,3S,5(2S),5S]-5-[[5-Oxo-1-(phenylmethyl)-2-pyrrolidinyl]methyl]-5-[(1H-imidazol-5-yl)methyl]cyclohexaneacetamide In the same manner as escribed in (a), reduction of the more polar diastereomer, [1S,3S,5(2S),5S]-5-[[5-oxo-1-(phenylmethyl)-2-pyrrolidinyl]methyl]-3-[[1-(phenylmethyl)-1 H-imidazol-5-yl]methyl]cyclohexaneacetamide, afforded [1S,3S,5(2S),5S]-5-[[5-oxo-1-(phenylmethyl)-2-pyrrolidinyl]methyl]-3-[(1H-imidazol-5-yl)methyl]cyclohexaneacetamide. $^1$H NMR (CDCl$_3$) δ 0.48–0.58 (m, 1 H, axial ring H), 0.88–0.95 (m. 1 H), 3.46 (m, 1 H, NCH), 3.92 and 4.98 (AB,J$_{gem}$=15 Hz, CH₂Ph), 5.39 and 5.62 (br s, 2 H, amide H) 6.75 (s, 1 H, imidazole ring H), 7.53 (s, 1 H, imidazole ring H), 7.20–7.35 (m, 5 H, phenyl). MS (EI) m/e 408 (M+). HRMS (EI): Calcd for $C_{24}H_{32}N_4O_2$ (M+) 408.2525. Obsd (M+) 408.2512. CD (ethanol) 233 ([Θ]=−1,700, max), 217 ([Θ]=+38,400, max), 211 ([Θ]=+35,200, min), 201 nm ([Θ]=+55,200°, max).

EXAMPLE 24

[1S,3RS,5(2S),5S]-3-(1H-Imidazol-5-ylmethyl)-5-[(5-oxo-2-pyrrolidinyl)methyl]cyclohexaneacetamide To a solution of [1S,3RS,5(2S),5S]-5-[[5-oxo-1-(phenylmethyl)-2-pyrrolidinyl]methyl]-3-[(1H-imidazol-5-yl)methyl]cyclohexaneacetamide (42 mg, 0.103 mmol) in 3 mL of tetrahydrofuran was added liquid ammonia (3 mL). To the solution was added sodium metal (23 mg, 1.0 mg-atom). The blue solution was stirred under reflux at −33° C. for 30 min and was quenched with solid ammonium chloride. The ammonia was allowed to evaporate and the residual paste was slurried with methanol and filtered. The methanol removed on a rotary evaporator, and the residue (22 mg) was chromatographed on an AG50W X 4 ion exchange resin eluting with water followed by 3% ammonium hydroxide to give 20 mg of salt-free [1S,3RS,5(2S),5S]-5-(1H-imidazol-5-yl-methyl)-3-[(5-oxo-2-pyrrolidinyl)-methyl]cyclo-hexaneacetamide. Further purification (Waters Delta Prep HPLC, reverse phase, Delta-Pak C-18/15μ, 7.8 mm×30 cm, eluting with a water to methanol gradient, followed by lyophilization of the fractions afforded 7.5 mg of pure [1S,3RS,5(2S),5S]-3-(1H-imidazol-5-yl-methyl)-5-[(5-oxo2-pyrrolidinyl)methyl]cyclohexaneacetamide as a white solid, mp 105°–110° C. ¹H NMR (CD₃OD) δ 0.6–0.75 (m, 1 H, axial ring H), 2.70 (br s, 2 H, CH₂-imidazole), 3.72 (m, 1 H, NCH), 6.81 and 7.56 (2s, 2 H, imidazole H's. MS (FAB) m/e 319 (M+H). HRMS (FAB): Calcd for $C_{17}H_{26}N_4O_2$ (M+H) 319.2134. Obsd (M+H) 319.2122.

EXAMPLE 25

[9R,9(5S)]-5-[(7-Methyl-1.4-dioxaspiro[4.5]dec-6-en-9-yl)methyl]-1-(phenylmethyl)-2-pyrrolidinone A solution of (5S,1R)-5-[(3-methyl-5-oxo-3-cyclohexen-1-yl)methyl]-1-(phenylmethyl)-2-pyrrolidinone (0.63 g, 212 mmol) in 20 mL of toluene containing 1.5 mL of ethylene glycol and p-toluenesulfonic acid (about. 10 mg) was heated to reflux under a water separator for 6 h. The solution was washed with 10% potassium carbonate and water, and was dried over Na₂SO₄. The solvent was removed on a rotary evaporator, and the crude product was chromatographed on silica gel, eluting with ethyl acetate to give 0.47 g (65% yield) of [9R,9(5S)]-5-[(7-methyl-1.4-dioxaspiro[4.5]dec-6-en-9-yl)methyl]-1-(phenylmethyl)-2-pyrrolidinone. ¹H NMR (CDCl₃) δ 0.95–2.6 (m, 11 H, CH and CH₂), 3.45 (br s, 1 H, NCH), 3.8–4.1 (m, 3 H, ketal CH₂'s and half of CH₂Ph), 5.03 (half of AB, J=15 Hz, 2 H, CH₂Ph), 5.08 (s, 1 H, vinyl H), 7.15–7.4 (m, 5 H, phenyl).

EXAMPLE 26

[9R,9(5S)]-5-[(7-Methyl-1.4-dioxaspiro[4.5]dec-6-en-9-yl)methyl]-2-pyrrolidinone To a solution of [9R,9(5S)]-5-[7-methyl-1.4-dioxaspiro[4.5]dec-6-en-9-yl)methyl]-1-(phenylmethyl)-2-pyrrolidinone (0.745 g, 2.2 mmol) in 14 mL of tetrahydrofuran and 28 mL of liquid ammonia at reflux was added sodium metal pieces (0.25 g, 11.0 mg-atom) until a blue solution had formed. The mixture was stirred at reflux for 20 min and was quenched by the addition of solid ammonium chloride. The ammonia was allowed to evaporate and the mixture was diluted with methylene chloride, filtered, and concentrated to give 0.553 g of crude product. Chromatography of a 0.275 g-portion on silica gel (10 g) eluting with 4% methanol in ethyl acetate gave 0.15 g of [9R,9(5S)]-5-[(7-methyl-1.4-dioxaspiro[4.5]dec-6-en-9-yl)methyl]-2-pyrrolidinone together with 0.044 g of recovered [9R,9(2S)]-5-[(7-methyl-1.4-dioxaspiro[4.5]dec-6-en-9-yl)methyl]-1-(phenylmethyl)-2-pyrrolidinone. ¹H NMR (CDCl₃) δ 0.9–2.6 (m, 14 H, CH and CH₂'s), 3.6–4.05 (m, 5 H, NCH and ketal CH₂'s), 5.32 (s, 1 H, vinyl H), 5.94 (s, 1 H, NH).

EXAMPLE 27

[9R,9(5S)]-1-[(4-Methoxyphenyl)methyl]-5-[(7-methyl-1,4-dioxaspiro[4.5]dec-6-en-9-yl)methyl]-2-pyrrolidinone To a suspension of sodium hydride (80 mg of 60% dispersion, 2.0 mmol) in 10 mL of toluene was added [9R,9(5S)]-5-[(7-methyl-1,4-dioxaspiro[4.5]dec-6-en-9-yl)methyl]-2-pyrrolidinone (210 mg, 84 mmol) and 4-methoxybenzyl chloride (300 mg, 1.92 mmol) and the mixture was heated to 100° C. for 1 h. The mixture was cooled, poured into water, and extracted with methylene chloride. The combined extracts were washed with brine, dried over Na₂SO₄, and the solvent was removed on a rotary evaporator. The residue was chromatographed on silica gel (15 g), eluting with ethyl acetate to give 150 mg of [9R,9(5S)]-1-[(4-methoxyphenyl)methyl]-5-[(7-methyl-1,4-dioxaspiro[4.5]dec-6-en-9-yl)methyl]-2-pyrrolidinone ¹H NMR (CDCl₃) δ 1.1–2.6 (m, 14 H, CH and CH₂'s), 3.44 (m, 1 H, NCH), 3.82 (s, 3 H, OCH₃), 3.8–4.02 (m, 5 H, ketal CH₂'s and part of CH₂Ar), 4.97 (part of AB, J=15 Hz, 1 H, part of CH₂Ar), 5.19 (s, 1 H, vinyl H), 6.86 and 7.18 (AB,J=8.5 Hz, 4 H, aromatic H).

Example 28

[5S,1R]-1-[(4-Methoxyphenyl)methyl]-5-[3-methyl-5-oxo-3-cyclohexen-1-yl)methyl]-2-pyrrolidinone A mixture of the [9R,9(5S)]-1-[(4-methoxyphenyl)-methyl]-5-[(7-methyl-1,4-dioxaspiro[4.5]dec-6-en-9-yl)methyl]-2-pyrrolidinone (260 mg, 0.7 mmol) and Amberlyst15 ion exchange resin (180 mg) in 20 mL of 2% aqueous acetone was allowed to stir overnight at room temperature. The mixture was filtered and the solvent was removed on a rotary evaporator to give 210 mg of crude product. The material was chromatographed on silica gel (7 g) eluting with ethyl acetate to afford 190 mg of [5S,1R]-1-[(4-methoxyphenyl)methyl]-5-[3-methyl-5-oxo-3-cyclohexen-1-yl)methyl]-2-pyrrolidinone. ¹H NMR (CDCl₃) δ 1.23–2.55 (m, 11 H, CH and CH₂'s), 1.96 (s, 3 H, vinyl CH₃), 3.45 (m, 1 H, NCH), 3.85 and 4.94 (AB,J=15 Hz, 2 H, CH₂Ph), 5.89 (s, 1 H, vinyl H), 6.85 and 7.16 (AB,J=8.5 Hz, 4 H, aromatic H).

The [9R,9(5S)]-1-[(4-methoxyphenyl)methyl]-5-[3-methyl-5-oxo-3-cyclohexen-1-yl)methyl]-2-pyrrolidinone was converted following the methods described in example 12–14 to give [1R,3R,5S,5(2S)]-3-methyl-5-[[5-oxo-1-[(4-methoxyphenyl)methyl]-2-pyrrolidinyl]methyl]cyclohexaneacetamide. ¹H NMR (CDCl₃) δ 0.3–2.5 (m, CH and CH₂'s), 0.87 (d,J=6 Hz, 3 H ring CH₃), 3.44 (m, 1 H, NCH), 3.80 (s, 3 H, OCH₃), 3.87 and 4.94 (AB,J=15 Hz, 2 H, CH$_2$Ph), 5.1-5.35 (m, 2 H, NH$_2$), 6.84 and 7.14 (AB,J=9 Hz, 4 H, aromatic H).

In an analogous manner, the [9R,9(5S)]-5-[(7-methyl-1.4-dioxaspiro[4.5]dec-6-en-9-yl)methyl]-2-pyrrolidinone was reacted with other alkyl and aralkyl halides following the methods described in examples 27, 28 and 12-14 to afford the products listed in Table I.

TABLE I 1-substituted-[1R, 3R, 5S, 5(2S)]-3-methyl-5-[[5-oxo-2-pyrrolidinyl]methyl]cyclohexaneacetamides.

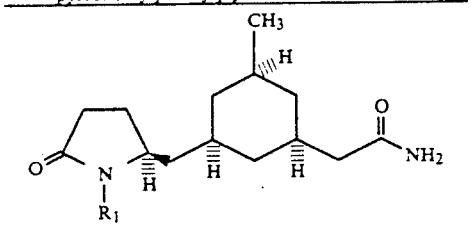

| Example | Starting halide | R$_1$ |
|---|---|---|
| 29 | 4-chlorobenzyl chloride | Cl—⟨⟩—CH$_2$— |
| 30 | methyl iodide | CH$_3$ |

EXAMPLE 31

(5S,1R)-5-[(5-Oxo-3-cyclohexen-1-yl)methyl]-1-(phenylmethyl)-2-pyrrolidinone

To a solution of (5S,1R)-5-[(3-ethoxy-5-oxo-3-cyclohexen-1-yl)methyl)]-1-(phenylmethyl)-2-pyrrolidinone (0.51 g, 1.56 mmol) in 15 mL of methanol at 0° C. was added ceric chloride (0.745 g, 3.0 mmol). To the mixture was added in portions sodium borohydride (0.115 g, 3.0 mmol), and the mixture was stirred for 30 min at 0° C. Water (15 mL) was added and the solution was extracted with methylene chloride. The combined extracts were washed with brine, dried over sodium sulfate, and concentrated on a rotary evaporator to give 0.47 g of the reduction product. This material was dissolved in tetrahydrofuran (10 mL) and 3N HCl (10 mL) was added. The solution was heated to 50° C. for 1 h, cooled to room temperature, and extracted with methylene chloride. The combined extracts were washed with brine, dried over sodium sulfate, and evaporated to give 0.44 g of (5S,1R)-5-[(5-oxo-3-cyclohexen-1-yl)methyl]-1-(phenylmethyl)-2-pyrrolidinone as a gummy oil.

EXAMPLE 32

[1R,3S,3(2S)]-3-[[5-Oxo-1-(phenylmethyl)-2-pyrrolidinyl]methyl]cyclohexaneacetamide Following the procedure of Examples 12-14, 0.44 g of (5S,1R)-5-[(5-oxo-3-cyclohexen-1-yl)methyl]-1-(phenylmethyl)-2-pyrrolidinone was converted to [1R,3S,3(2S)]-3-[[5-oxo-1-(phenylmethyl)-2-pyrrolidinyl]methyl]-cyclohexaneacetamide via the reaction with ethyl trimethylsilylacetate followed by catalytic hydrogenation, saponification, and conversion to the amide, [1R,3S,3(2S)]-3-[[5-oxo-1-(phenylmethyl)-2-pyrrolidinyl]methyl]-cyclohexaneacetamide. There was obtained 0.26 g of [1R,3S, 3(2S)]-3-[[5-oxo-1-(phenylmethyl)-2-pyrrolidinyl]methyl]-cyclohexaneacetamide after chromatography on silica gel, eluting with 2-4% methanol in chloroform. The product also contained some of the 1S diastereomer by NMR.

EXAMPLE 33

[1S,5R,5(2S)]-3-(Phenylmethylene)-5-[[5-oxo-1-(phenylmethyl)-2-pyrrolidinyl]methyl]cyclohexaneacetic acid ethyl ester To a suspension of benzyltriphenylphosphonium bromide (0.43 g, 1.0 mmol) in 15 mL of toluene at 0° C. was added n-butyllithium (0.4 mL of a 2.5M solution in hexanes). The mixture was stirred for 1 h at ice bath temperature, and the ketoester, [1S,5S,5(2S)]-3-oxo-5-[[5-oxo-1-(phenylmethyl)-2-pyrrolidinyl]methyl]cyclohexaneacetic acid ethyl ester (0.18 g, 0.5 mmol) was added. The mixture was then heated to reflux overnight, cooled, poured into water, and extracted with ethyl acetate. The combined extracts were washed with brine and dried over sodium sulfate. The solvent was removed and the residue chromatographed on silica gel, eluting with methylene chloride followed by ethyl acetate to give 0.02 g of the benzylidene compound, [1S,5R, 5(2S)]-3-(phenylmethylene)-5-[[5-oxo-1-(phenylmethyl)-2-pyrrolidinyl]methyl]cyclo-hexaneacetic acid ethyl ester.. $^1$H NMR (CDCl$_3$) δ 0.8–0.95 (m, 3 H, CH$_3$), 3.9–4.2 (m, 2 H, CH$_2$CO and 1 H, CH$_2$Ph), 4.92 and 5.00 (2d, J=12 Hz, 1 H, CH$_2$Ph), 6.29 (s, 1 H, vinyl H), 7.1–7.4 (5 H, aromatic H). MS (EI) m/e 445 (m$^+$).

EXAMPLE 34

[1S,3RS,5(2S),5S]-5-[[5-Oxo-1-(phenylmethyl)-2-pyrrolidinyl]methyl]-3-[[1-(phenylmethyl)-1H-imidazol-5-yl]methyl]cyclohexane-N-methyl acetamide and [1S,3RS,5(2S),5S]-3-[[5-Oxo-1-(phenylmethyl)-2-pyrrolidinyl]methyl]-5-[(1H-imidazol-5-yl)methyl]cyclohexane-N-methylacetamide The procedure of example 21 was followed, starting from [1S,5R,5(2S)]-5-[[5-oxo-1-(phenylmethyl)-2-pyrrolidinyl]methyl]-3-[[1-(phenylmethyl)-1H-imidazol-5-yl]methylene]cyclohexaneacetic acid ethyl ester (0.69 g, 1.31 mmol), performing the saponification of the ester and formation of the active ester with ethyl chloroformate and triethylamine as described. To the solution containing the active ester was added 15 mL of anhydrous methylamine (in place of ammonia, as in example 21). The solution was stirred for 30 min at room temperature, and concentrated. The residue was chromatographed to afford 80 mg of the intermediate [1S,5R,5(2S)]-5-[[5-oxo-1-(phenylmethyl)-2-pyrrolidinyl]-methyl]-5-[[1-(phenylmethyl)-1H-imidazol-5-yl]methylene]cyclohexane-N-methylacetamide after chromatography. Catalytic hydrogenation of the compound over 10% palladium on carbon at 1 atm of hydrogen as in example 22 afforded 60 mg of [1S, 3RS,5(2S),5S]-5-[[5-oxo-1-(phenylmethyl)-2-pyrrolidinyl]methyl]-3-[[1-(phenylmethyl)-1H-imidazol-5-yl]methyl]cyclohexane-N-methylacetamide. Reduction as in example 23 at 50° C. and at 150 psi of hydrogen for 24 hr gave 30 mg of the desired [1S,3RS,5(2S),5S]-5-[[5-oxo-1-(phenylmethyl)-2-pyrrolidinyl]methyl]-3-[(1H-imidazol-5-yl)methyl]cyclohexane-N-methylacetamide as a solid after chromatography on silica gel eluting with the lower phase of a mixture prepared by shaking 90 parts CHCl$_3$, 30 parts CH$_3$OH, 10 parts water and 6 parts acetic acid. The product had mp=90°-93° C. HRMS (FAB): Calcd for C$_{25}$H$_{34}$N$_4$O$_2$ (M+H) 422.2682. Obsd (M+H) 422.2656

EXAMPLE 35

[1R,3R,5(2S)]-3-[1-(Phenylmethyl)]-5-[[5-oxo-1-(phenylmethyl)-2-pyrrolidinyl]methyl]cyclohexaneacetamide The benzylidine derivative, [1S,5R,5(2S)]-3-(phenylmethylene)-5-[[5-oxo-1-(phenylmethyl)-2-pyrrolidinyl]methyl]cyclo-hexaneacetic acid ethyl ester (0.02 g), was saponified and converted to the amide following the procedure of Example 14 to give, after chromatography on silica gel, 8.0 mg of the desired benzylidene amide. Catalytic hydrogenation of the amide in methanol solution over 10% palladium on carbon afforded 4 mg of the desired benzyl derivative, [1R,3R,5(2S)]-3-[1-(Phenylmethyl)]-5-[[5-oxo-1-(phenylmethyl)-2-pyrrolidinyl]methyl]cyclo-, hexaneacetamide. $^1$H NMR (CDCl$_3$) δ 0.4–0.65 (m, 2 H, axial H), 2.3–2.6 (m, 2 H, CH$_2$CO), 3.4–3.5 (m, 1 H, CHN), 3.94 and 4.95 (dd, 2 H, PhCH$_2$), 5.25 (br d, J=15 Hz, CONH$_2$), 7.05–7.35 (m, 10 H, Aromatic). MS (EI) m/e 447 (M+).

EXAMPLE 36

[1S,3R,5(2S),5S]-3-[(1-Methyl-1H-imidazol-5-yl)methyl-5-[[5-oxo-1-(phenylmethyl)-2-pyrrolidinyl]methyl]cyclohexaneacetamide and [1S,3R,5(2S),5S]-3-[(1-methyl-1H-imidazol-4-yl)methyl]-5-[[5-oxo-1-(phenylmethyl)-2-pyrrolidinyl]methyl]cyclohexaneacetamide To a solution of [1S,3R,5(2S),5S]-3-[(1H-imidazol-5-yl)methyl]-5-[[5-oxo-1-(phenylmethyl)-2-pyrrolidinyl]methyl]-5-cyclohexaneacetamide (0.044 g) in 1 mL of methylene chloride was added excess 4-dimethylaminopyridine and pyridine with stirring in an ice bath. Acetyl chloride (17 mg, 20 equiv.) was added and the mixture was allowed to warm slowly to room temperature and was then poured into water and extracted with methylene chloride. The combined extracts were washed with brine, dried over sodium sulfate, and evaporated to give 0.055 g of crude acetate. The crude product was chromatographed on silica gel, eluting with the lower phase of a mixture prepared by shaking 90 parts chloroform, 15–30 parts methanol, 10 parts water, and 6 parts of acetic acid to give the acetylated imidazole compounds. The mixture (5 mg) was treated with excess methyl iodide in acetonitrile at reflux for 2 h, followed by evaporation of the solvent and warming the residue with 2.5N sodium hydroxide at reflux for 30 min. After neutralization, the solution was extracted with methylene chloride, and the combined extracts were dried over sodium sulfate and evaporated to give approximately a 1:15 mixture of the two methylated imidazole compounds, [1S,3R,5(2S),5S]-3-[(1-Methyl-1H-imidazol-5-yl)methyl]-5-[[5-oxo-1-(phenylmethyl)-2-pyrrolidinyl]methyl]cyclohexaneacetamide and [1S,3R,5(2S),5S]-3-[(1-methyl-1H-imidazol-4-yl)methyl]-5-[[5-oxo-1-(phenylmethyl)-2-pyrrolidinyl]methyl]cyclohexaneacetamide $^1$H NMR (CDCl$_3$) δ 3.50 and 3.60 (2s, 3 H, CH$_3$-imidazole-N), 3.90 and 4.95 (dd, J$_{gem}$=12 Hz, 2 H, CH$_2$Ph), 6.55 and 6.72 (2 br s, 2 H, vinyl H). 7.15–7.35 (m, 5 H, aromatic). MS (EI) m/e 422 (m+).

WET GRANULATION FORMULATION

| Ingredients | mg/tablet | | | |
|---|---|---|---|---|
| 1. [1R,3R,5S,5(5S)]-3-methyl-5-[[5-oxo-1-(phenylmethyl)-2-pyrrolidinyl]methyl]-cyclohexaneacetamide | 0.01 | 0.5 | 5.0 | 25.0 |
| 2. Lactose Anhydrous DTG | 106.99 | 106.5 | 102.0 | 118.0 |
| 3. Avicel PH 102 | 15.0 | 15.0 | 15.0 | 25.0 |
| 4. Modified Starch | 7.0 | 7.0 | 7.0 | 10.0 |
| 5. Magnesium Starch | 1.0 | 1.0 | 1.0 | 2.0 |
| Total | 130.0 | 130.0 | 130.0 | 180.0 |

Manufacturing Procedure:

1. Dissolve item 1 in a suitable solvent such as alcohol.
2. Spread the solution in Step 1 over item 2, dry.
3. Add item 3 and 4 and mix for 10 minutes.
4. Add magnesium stearate and mix for 3 minutes and compress.

CAPSULE FORMULATION

| Ingredients | mg/capsule | | | |
|---|---|---|---|---|
| 1. [1R,3R,5S,(5S)]-3-methyl-5-[[5-oxo-1-(phenylmethyl)-2-pyrrolidinyl]methyl]-cyclohexaneacetamide | 0.01 | 0.5 | 5.0 | 25.0 |
| 2. Lactose Hydrous | 168.99 | 168.5 | 159.0 | 123.0 |
| 3. Corn Starch | 20.0 | 20.0 | 25.0 | 35.0 |
| 4. Talc | 10.0 | 10.0 | 10.0 | 15.0 |
| 5. Magnesium Stearate | 1.0 | 1.0 | 1.0 | 2.0 |
| Total | 200.0 | 200.0 | 200.0 | 200.0 |

Manufacturing Procedure

1. Mix items 1, 2 and 3 in a suitable mixture for 30 minutes.
2. Add items 4 and 5 and mix for 3 minutes
3. Fill into suitable capsule

I claim:

1. A compound of the formula

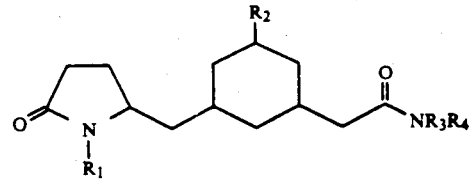

wherein R$_1$ is hydrogen, lower alkyl or aryl-lower alkyl; R$_2$ is hydrogen, lower alkyl, aryl, aryl-lower alkyl,

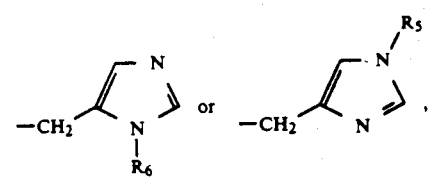

wherein R$_5$ and R$_6$ are hydrogen, lower alkyl or aryl-lower alkyl; R$_3$ and R$_4$, independently, are hydrogen, lower alkyl or aryl-lower alkyl;

or an enantiomer, diastereomer, or racemate thereof, and, when R$_2$ is

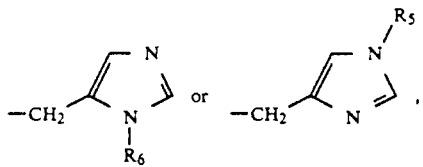

a pharmaceutically acceptable acid addition salt thereof.

2. A compound, in accordance with claim 1, wherein $R_1$ is hydrogen, lower alkyl or aryl-lower alkyl; $R_2$ is hydrogen, lower alkyl, or

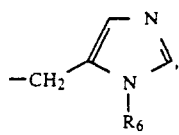

wherein $R_6$ is hydrogen or aryl-lower alkyl; $R_3$ and $R_4$, independently, are hydrogen or lower alkyl or an enantiomer thereof, or, when $R_2$ is

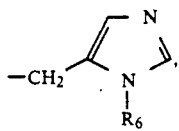

a pharmaceutically acceptable acid addition salt thereof.

3. A compound, in accordance with claim 2, wherein $R_1$ is hydrogen or aryl-lower alkyl; $R_2$ is lower alkyl or

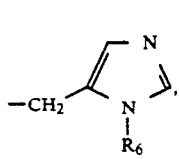

wherein $R_6$ is hydrogen or aryl-lower alkyl; $R_3$ and $R_4$ are hydrogen or, when $R_2$ is

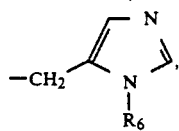

a pharmaceutically acceptable acid addition salt thereof.

4. A compound of the formula

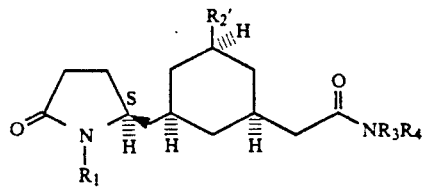

wherein $R_1$ is hydrogen, lower alkyl or aryl-lower alkyl; $R_2'$ is hydrogen, alkyl or aryl-lower alkyl; $R_3$ and $R_4$, independently, are hydrogen, lower alkyl or aryl-lower alkyl, or its enantiomer or racemate thereof.

5. A compound, in accordance with claim 4, wherein $R_1$ is hydrogen or aryl-lower alkyl; $R_2$ is hydrogen or lower alkyl; $R_3$ and $R_4$ are hydrogen, or its enantiomer.

6. A compound of the formula

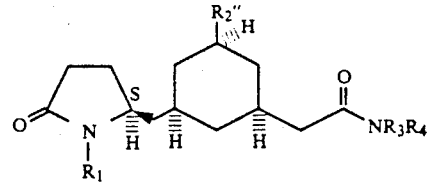

wherein $R_1$ is hydrogen, lower alkyl or aryl-lower alkyl; $R_2''$ is

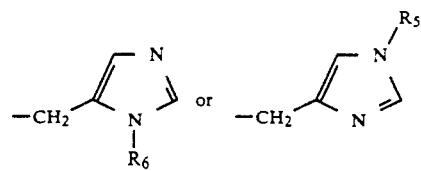

wherein $R_5$ and $R_6$ are hydrogen, lower alkyl or aryl-lower alkyl; and $R_3$ and $R_4$, independently, are hydrogen, lower alkyl or aryl-lower alkyl; or its enantiomer or racemate thereof, or a pharmaceutically acceptable acid addition salt thereof.

7. A compound, in accordance with claim 6, wherein $R_1$ is hydrogen or aryl-lower alkyl; $R_2''$ is

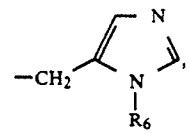

wherein $R_6$ is hydrogen or aryl lower-alkyl; and $R_3$ and $R_4$ are hydrogen or its enantiomer, or a pharmaceutically acceptable acid addition salt thereof.

8. A compound, in accordance with claim 1, [1R,3R,5S,5(2S)]-3-methyl-5-[[5-oxo-1-(phenylmethyl)-2-pyrrolidinyl]methyl]cyclohexaneacetamide.

9. A compound, in accordance with claim 1, [1R,3R,5S,5(2S)]-3-methyl-5-[[5-oxo-2-pyrrolidinyl]methyl]cyclohexaneacetamide.

10. A compound, in accordance with claim 1, [1R,3R,5S,5(2S)]-3-methyl-5-[[5-oxo-1-[(4-methoxyphenyl)methyl]-2-pyrrolidinyl]methyl]cyclohexaneacetamide.

11. A compound, in accordance with claim 1, [1R,3R,5S,5(2S)]-3-methyl-5-[[5-oxo-1-[(4-chlorophenyl)methyl]-2-pyrrolidinyl]methyl]cyclohexaneacetamide.

12. A compound, in accordance with claim 1, [1S,3R,5(2S),5S]-3-[[1-(phenylmethyl)-1H-imidazol-5-yl]methyl]-5-[[5-oxo-1-(phenylmethyl)-2-pyrrolidinyl]methyl]cyclohexaneacetamide.

13. A compound, in accordance with claim 1, [1S,3R,5(2S),5S]-3-[(1H-imidazol-5-yl)methyl]-5-[[5-oxo-1-(phenylmethyl)-2-pyrrolidinyl]methyl]cyclohexaneacetamide.

14. A compound, in accordance with claim 1, [1S,3R,5(2S),5S]-3-(1H-imidazol-5-yl-methyl)-5-[(5-oxo-2-pyrrolidinyl)methyl]cyclohexaneacetamide.

15. A compound, in accordance with claim 1, [1R,3S,3(2S)]-3-[[5-oxo-1-(phenylmethyl)-2-pyrrolidinyl]methyl]cyclohexaneacetamide.

16. A compound, in accordance with claim 1, [1S,3R,5(2S),5S]-3-[(1H-imidazol-5-yl)methyl]-5-[[5-oxo-1-(phenylmethyl)-2-pyrrolidinyl]methyl]cyclohexane-N-methylacetamide.

17. A compound, in accordance with claim 1, [1S,3R,5(2S),5S]-3-[[1-(phenylmethyl)-1H-imidazol-5-yl)methyl]-5-[[5-oxo-1-(phenylmethyl)-2-pyrrolidinyl]methyl]cyclohexane-N-methylacetamide.

18. A compound, in accordance with claim 1, [1S,3R,5(2S),5S]-3-[(1-methyl-1H-imidazol-5-yl)methyl]-5-[[5-oxo-1-(phenylmethyl)-2-pyrrolidinyl]methyl]cyclohexaneacetamide.

19. A compound, in accordance with claim 1, [1S,3R,5(2S),5S]-3-[(1-methyl-1H-imidazol-4-yl)methyl]-5-[[5-oxo-1-(phenylmethyl)-2-pyrrolidinyl]methyl]cyclohexaneacetamide.

20. A pharmaceutical composition comprising an effective amount of a compound of the formula

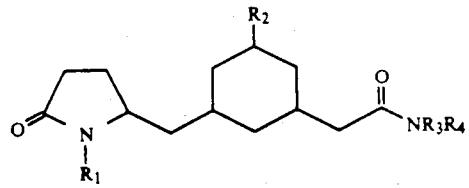

wherein $R_1$ is hydrogen, lower alkyl or aryl-lower alkyl; $R_2$ is hydrogen, lower alkyl, aryl, aryl-lower alkyl,

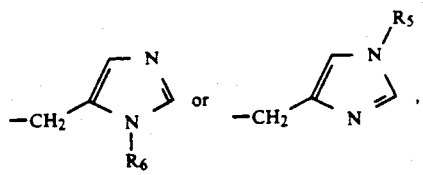

wherein $R_5$ and $R_6$ are hydrogen, lower alkyl or aryl-lower alkyl; $R_3$ and $R_4$, independently, are hydrogen, lower alkyl or aryl-lower alkyl;
or an enantiomer, diastereomer, or racemate thereof, and, when $R_2$ is

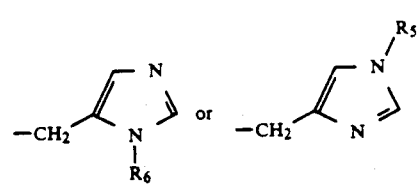

a pharmaceutically acceptable acid addition salt thereof, and an inert carrier.

21. A pharmaceutical composition, in accordance with claim 20, wherein $R_1$ is hydrogen, lower alkyl or aryl-lower alkyl; $R_2$ is hydrogen, lower alkyl, or

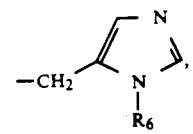

wherein $R_6$ is hydrogen or aryl-lower alkyl; and $R_3$ and $R_4$, independently, are hydrogen or lower alkyl
or an enantiomer thereof, or, when $R_2$ is

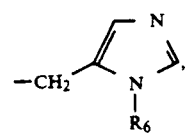

a pharmaceutically acceptable acid addition salt thereof and an inert carrier.

22. A pharmaceutical composition, in accordance with claim 21, wherein $R_1$ is hydrogen or aryl-lower alkyl; $R_2$ is lower alkyl or

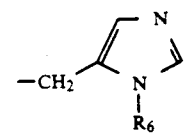

wherein $R_6$ is hydrogen or aryl-lower alkyl; and $R_3$ and $R_4$ are hydrogen.

23. A pharmaceutical composition comprising an effective amount of a compound of the formula

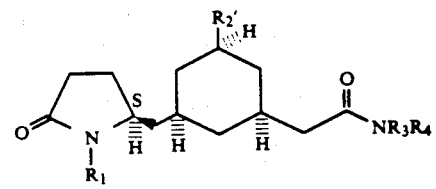

wherein $R_1$ is hydrogen, lower alkyl or aryl-lower alkyl; $R_2'$ is hydrogen, alkyl or aryl-lower alkyl; and $R_3$ and $R_4$, independently, are hydrogen, lower alkyl or aryl-lower alkyl,
or its enantiomer or racemate thereof, and an inert carrier.

24. A pharmaceutical composition, in accordance with claim 23, wherein $R_1$ is hydrogen or aryl-lower alkyl; $R_2'$ is hydrogen or lower alkyl; $R_3$ and $R_4$ are hydrogen, or its enantiomer.

25. A pharmaceutical composition comprising an effective amount of a compound of the formula

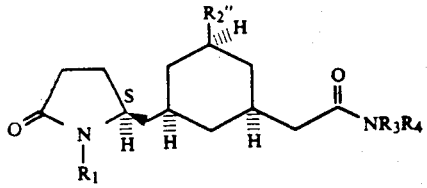

wherein $R_1$ is hydrogen, lower alkyl or aryl-lower alkyl; $R_2''$ is

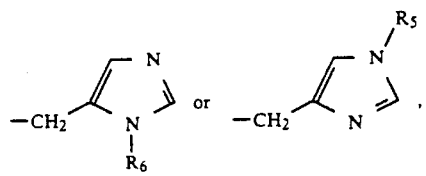

wherein R$_5$ and R$_6$ are hydrogen, lower alkyl or aryl-lower alkyl; and R$_3$ and R$_4$, independently, are hydrogen, lower alkyl or aryl-lower alkyl;

or its enantiomer or racemate thereof, or a pharmaceutically acceptable acid addition salt and an inert carrier.

26. A pharmaceutical composition, in accordance with claim 25, wherein R$_1$ is hydrogen or aryl-lower alkyl; R$_2''$ is

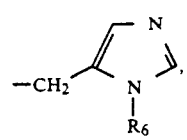

wherein R$_6$ is hydrogen or aryl lower-alkyl; and R$_3$ and R$_4$ are hydrogen or its enantiomer, or a pharmaceutically acceptable acid addition salt thereof.

27. A pharmaceutical composition, in accordance with claim 20, wherein the compound of formula I is [1R,3R,5S,5(2S)]-3-Methyl-5-[[5-oxo-1-(phenylmethyl)-2-pyrrolidinyl]methyl]cyclohexaneacetamide.

28. A pharmaceutical composition, in accordance with claim 20, wherein the compound of formula I is [1R,3R,5S,5(2S)]-3-Methyl-5-[[5-oxo-2-pyrrolidinyl]-methyl]cyclohexaneacetamide.

29. A pharmaceutical composition, in accordance with claim 20, wherein the compound of formula I is [1S,3R,5(2S),5S]-3-[[1-(phenylmethyl)-1H-imidazol-5-yl]methyl]-5-[[5-oxo-1-(phenylmethyl)-2-pyrrolidinyl]-methyl]cyclohexaneacetamide.

30. A pharmaceutical composition, in accordance with claim 20, wherein the compound of formula I is [1S,3R,5(2S),5S]-3-[(1H-imidazol-5-yl)methyl]-5-[[5-oxo-1-(phenylmethyl)-2-pyrrolidinyl]methyl]cyclohexaneacetamide.

31. A pharmaceutical composition, in accordance with claim 20, wherein the compound of formula I is [1S,3R,5(2S),5S]-3-(1H-imidazol-5-yl-methyl)-5-[(5-oxo-2-pyrrolidinyl)methyl]cyclohexaneacetamide.

32. A method of treating memory deficits associated with Alzheimer's disease or age-associated memory impairment which comprises administering to a host requiring such treatment an effective amount of

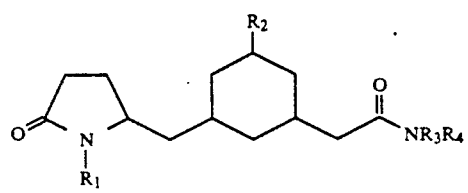   I wherein R$_1$ is hydrogen, lower alkyl or aryl-lower alkyl; R$_2$ is hydrogen, lower alkyl, aryl, aryl-lower alkyl,

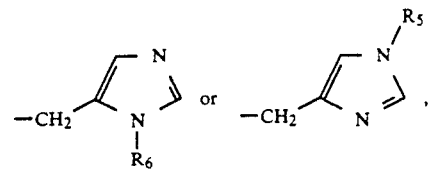

wherein R$_5$ and R$_6$ are hydrogen, lower alkyl or aryl-lower alkyl; R$_3$ and R$_4$, independently, are hydrogen, lower alkyl or aryl-lower alkyl;

or an enantiomer, diastereomer, or racemate thereof, and, when R$_2$ is

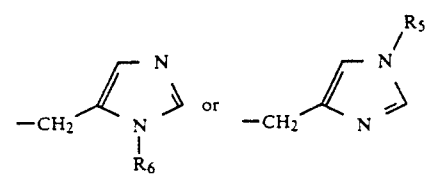

a pharmaceutically acceptable acid addition salt thereof.

33. A method, in accordance with claim 32, wherein R$_1$ is hydrogen, lower alkyl or aryl-lower alkyl; R$_2$ is hydrogen, lower alkyl, or

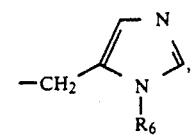

wherein R$_6$ is hydrogen or aryl-lower alkyl; R$_3$ and R$_4$, independently, are hydrogen or lower alkyl or an enantiomer thereof, or, when R$_2$ is

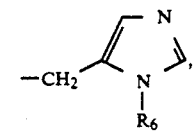

a pharmaceutically acceptable acid addition salt thereof.

34. A method, in accordance with claim 33, wherein R$_1$ is hydrogen or aryl-lower alkyl; R$_2$ is lower alkyl or

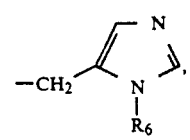

wherein R$_6$ is hydrogen or aryl-lower alkyl; R$_3$ and R$_4$ are hydrogen.

35. A method of treating memory deficits associated with Alzheimer's disease or age-associated memory impairment which comprises administering to a host requiring such treatment an effective amount of a compound of the formula

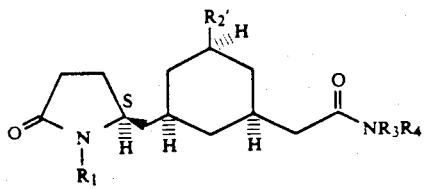

I-A wherein $R_1$ is hydrogen, lower alkyl or aryl-lower alkyl; $R_2'$ is hydrogen, alkyl or aryl-lower alkyl; and $R_3$ and $R_4$, independently, are hydrogen, lower alkyl or aryl-lower alkyl, or its enantiomer or racement thereof.

36. A method, in accordance with claim 35, wherein $R_1$ is hydrogen or aryl-lower alkyl; $R_2$ is hydrogen or lower alkyl; $R_3$ and $R_4$ are hydrogen, or its enantiomer.

37. A method of treating memory deficits associated with Alzheimer's disease or age-associated memory impairment which comprises administering to a host requiring such treatment an effective amount of a compound of the formula

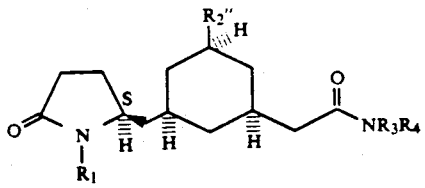

I-B wherein $R_1$ is hydrogen, lower alkyl or aryl-lower alkyl; $R_2''$ is

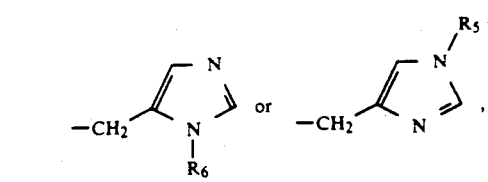

wherein $R_5$ and $R_6$ are hydrogen, lower alkyl or aryl-lower alkyl; and $R_3$ and $R_4$, independently, are hydrogen, lower alkyl or aryl-lower alkyl;

or its enantiomer or racemate thereof, or a pharmaceutically acceptable acid addition salt thereof.

38. A method, in accordance with claim 37, wherein $R_1$ is hydrogen or aryl-lower alkyl; $R_2''$ is

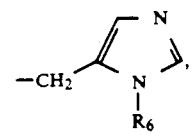

wherein $R_6$ is hydrogen or aryl lower-alkyl; and $R_3$ and $R_4$ are hydrogen or its enantiomer, or a pharmaceutically acceptable acid addition salt thereof.

39. A method, in accordance with claim 32, wherein the compound of formula I is [1R,3R,5S,5(2S)]-3-Methyl-5-[[5-oxo-1-(phenylmethyl)-2-pyrrolidinyl]methyl]-cyclohexaneacetamide.

40. A method, in accordance with claim 32, wherein the compound of formula I is [1R,3R,5S,5(2S)]-3-Methyl-5-[[5-oxo-2-pyrrolidinyl]methyl]cyclohexaneacetamide.

41. A method, in accordance with claim 32, wherein the compound of formula I is [1S,3R,5(2S),5S]-3-[[1-(phenylmethyl)-1H-imidazol-5-yl]methyl]-5-[[5-oxo-1-(phenylmethyl)-2-pyrrolidinyl]methyl]cyclohexaneacetamide.

42. A method, in accordance with claim 32, wherein the compound of formula I is [1S,3R,5(2S),5S]-3-[(1H-imidazol-5-yl)methyl]-5-[[5-oxo-1-(phenylmethyl)-2-pyrrolidinyl]methyl]cyclohexaneacetamide.

43. A method, in accordance with claim 32, wherein the compound of formula I is [1S,3R,5(2S),5S]-3-(1H-imidazol-5-yl-methyl)-5-[(5-oxo-2-pyrrolidinyl)methyl]-cyclohexaneacetamide.

* * * * *